(12) United States Patent
Benker et al.

(10) Patent No.: US 10,534,869 B2
(45) Date of Patent: *Jan. 14, 2020

(54) METHOD FOR DESIGNING AND MANUFACTURING A BONE IMPLANT

(71) Applicants: DePuy Synthes Products, Inc., Raynham, MA (US); Wolfgang Hoeller, Linz (AT)

(72) Inventors: Emanuel Benker, Oberdorf (CH); Andre Furrer, Luterkofen (CH); Wolfgang Hoeller, Linz (AT)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/220,383

(22) Filed: Dec. 14, 2018

(65) Prior Publication Data
US 2019/0130054 A1 May 2, 2019

Related U.S. Application Data

(63) Continuation of application No. 14/146,499, filed on Jan. 2, 2014, now Pat. No. 10,192,002.
(Continued)

(51) Int. Cl.
*G06G 7/48* (2006.01)
*G06F 17/50* (2006.01)
(Continued)

(52) U.S. Cl.
CPC .......... *G06F 17/50* (2013.01); *A61B 17/8071* (2013.01); *A61B 34/10* (2016.02);
(Continued)

(58) Field of Classification Search
None
See application file for complete search history.

(56) References Cited

U.S. PATENT DOCUMENTS

| 5,378,154 A | 1/1995 | Van Der Zel |
| 5,768,134 A | 6/1998 | Swaelens et al. |

(Continued)

FOREIGN PATENT DOCUMENTS

| EP | 0756735 B1 | 8/1998 |
| JP | 2006-263241 A | 10/2006 |

(Continued)

OTHER PUBLICATIONS

Schmutz Beat et al: "Fit Assessment of Anatomic Plates for the Distal Medial Tibia", Journal of Orthopaedic Trauma Journal of Orthopaedic Trauma, Jan. 1, 2008 (Jan. 1, 2008), pp. 258-263.

(Continued)

*Primary Examiner* — Rehana Perveen
*Assistant Examiner* — Nithya J. Moll
(74) *Attorney, Agent, or Firm* — BakerHostetler

(57) ABSTRACT

An anatomical implant application, such as a bone implant application for instance, can receive an anatomical image that is representative of an anatomical structure. The anatomical implant application can generate an implant image that is associated with the anatomical structure. The generated implant image can define an inner surface that faces the anatomical image. A plurality of distances can be determined from respective locations of the inner surface of the implant image to the anatomical image in respective straight lines. The distances may represent a superimposition of the implant image over the anatomical image. The distances may be compared to a tolerance. The inner surface may be repositioned so as to change at least the select one of the distances. An implant, such as a bone implant for instance, may be fabricated in accordance with data that is associated with the implant image.

20 Claims, 28 Drawing Sheets

Related U.S. Application Data

(60) Provisional application No. 61/748,983, filed on Jan. 4, 2013.

(51) Int. Cl.
*A61B 17/80* (2006.01)
*A61B 34/10* (2016.01)
*A61B 17/00* (2006.01)

(52) U.S. Cl.
CPC ............... *A61B 2017/00526* (2013.01); *A61B 2034/108* (2016.02)

(56) References Cited

U.S. PATENT DOCUMENTS

| | | |
|---|---|---|
| 5,798,924 A | 8/1998 | Eufinger et al. |
| 6,932,842 B1 | 8/2005 | Litschko et al. |
| 6,978,188 B1 | 12/2005 | Christensen |
| 7,383,163 B2 | 6/2008 | Holberg |
| 7,603,192 B2 | 10/2009 | Martin et al. |
| 8,160,345 B2 | 4/2012 | Pavlovskaia et al. |
| 8,166,627 B2 | 5/2012 | Deffrennes |
| 8,177,822 B2 | 5/2012 | Medoff |
| 2007/0118055 A1 | 5/2007 | McCombs |
| 2008/0004633 A1* | 1/2008 | Arata ............... A61B 17/1764 606/130 |
| 2008/0195240 A1 | 8/2008 | Martin et al. |
| 2009/0149977 A1 | 6/2009 | Schendel |
| 2009/0274350 A1 | 11/2009 | Pavlovskaia et al. |
| 2009/0306801 A1* | 12/2009 | Sivak ................... A61F 5/0111 700/98 |
| 2010/0256479 A1 | 10/2010 | Park et al. |
| 2011/0269100 A1 | 11/2011 | Furrer et al. |
| 2011/0282473 A1 | 11/2011 | Pavlovskaia et al. |
| 2011/0288640 A1 | 11/2011 | Lal |
| 2012/0022604 A1 | 1/2012 | Polley et al. |
| 2012/0029574 A1 | 2/2012 | Furrer et al. |
| 2012/0106819 A1 | 5/2012 | Fernandez Oca |
| 2012/0141034 A1 | 6/2012 | Iannotti et al. |
| 2012/0148985 A1 | 6/2012 | Jung et al. |
| 2012/0150243 A9 | 6/2012 | Crawford et al. |
| 2012/0192401 A1 | 8/2012 | Pavlovskaia et al. |
| 2012/0276509 A1 | 11/2012 | Iannotti et al. |
| 2012/0285002 A1 | 11/2012 | Lin et al. |
| 2012/0289965 A1 | 11/2012 | Gelaude et al. |
| 2013/0345718 A1* | 12/2013 | Crawford ............. A61B 17/025 606/130 |
| 2015/0297916 A1* | 10/2015 | Chen .................... A61N 5/1039 600/1 |

FOREIGN PATENT DOCUMENTS

| | | |
|---|---|---|
| WO | 20121176886 A1 | 12/2012 |
| WO | 20131087082 A1 | 6/2013 |

OTHER PUBLICATIONS

Marie Cr0nskar: Journal of Medical and Biological Engineering, vol. 32, No. 2, Jan. 1, 2012 (Jan. 1, 2012), pp. 91-95.

Hernandez-Alfaro et al., "New protocol for three-dimensional surgical planning and CAD/CAM splint generation in orthognathic surgery: an in vitro and in vivo study,"International Journal of Oral & Maxillofacial Surgery, Mar. 2013, 10 pages.

Ciocca L et al: "A CAD/CAM-prototyped anatomical condylar prosthesis connected to a custom-made bone plate to support a fibula free flap", Medical & Biological Engineering & Computing, Springer, Berlin, DE, vol. 50, No. 7, Mar. 24, 2012 (Mar. 24, 2012), pp. 743-749.

Arndt P. Schulz: "Evidence Based Development of a Novel Lateral Fibula Plate (VariAx Fibula) Using a Real CT Bone Data Based Optimization Process During Device Development", The Open Orthopaedics Journal, vol. 6, No. 1, Jan. 19, 2012 (Jan. 19, 2012), pp. 1-7.

\* cited by examiner

METHOD FOR DESIGNING AND MANUFACTURING A BONE IMPLANT

CROSS REFERENCE TO RELATED APPLICATIONS

This Application is a continuation of U.S. application Ser. No. 14/146,499, filed Jan. 2, 2014, which claims the benefit of U.S. Provisional Patent Application Ser. No. 61/748,983, filed Jan. 4, 2013, the disclosures of which is hereby incorporated by reference as if set forth in its entirety herein.

BACKGROUND

Medical procedures often require an implantation of a device into a patient's body. For example, a bone implant, such as a bone plate, can be used to reconstruct a bone that has been fractured. Bone implants can also be implanted to alter bones that are not fractured, such as bones that are deformed. Often, bone plates are used in places where a cast cannot be used, such as the jaw, nose, eye sockets, and skull, although bone plates can be used to alter and repair a variety of bones. For example, a bone implant can hold a broken bone in place, allowing it to heal. A bone plate implant must be properly fitted to the bone in order to achieve the desired result, preferably while minimizing pain to the patient. For example, a bone implant that is not properly fitted may slow or nullify the healing process. Additionally, a bone implant that is not properly fitted may cause a patient unnecessary pain or discomfort. Current approaches to fitting a bone implant to a bone lack efficiency and precision.

SUMMARY

Techniques for implant design and manufacture are described herein. In one embodiment, a bone implant application may execute on a computing device. Such a computing device may optionally communicate with one or more other computing devices to send and receive information associated with bone implant features. The bone implant application may receive a bone image that is representative of a bone. For example, the bone may be corrected or repaired. The bone implant application may generate a bone implant image that is associated with the bone. The generated bone implant image may define an inner surface that faces the bone image. A plurality of distances may be determined from respective locations of the inner surface of the bone implant image to the bone image in respective straight lines. The distances may represent a superimposition of the bone implant image over the bone image. The distances may be compared to a tolerance. When at least a select one of the plurality of distances is not within the tolerance, the inner surface may be repositioned so as to change at least the select one of the distances.

In accordance with an embodiment, manufacturing data may be received that is associated with a bone implant image that was generated by a bone implant application. A bone implant may be fabricated in accordance with the received data. For instance, the bone implant image may be positioned in an image of raw material. The raw material may be shaped based on the image of raw material.

The foregoing summarizes only a few aspects of the present disclosure and is not intended to be reflective of the full scope of the present disclosure. Additional features and advantages of the disclosure are set forth in the following description, may be apparent from the description, or may be learned by practicing the invention. Moreover, both the foregoing summary and following detailed description are exemplary and explanatory and are intended to provide further explanation of the disclosure.

BRIEF DESCRIPTION OF THE DRAWINGS

The foregoing summary, as well as the following detailed description of example embodiments of the present disclosure, will be better understood when read in conjunction with the appended drawings. For the purposes of illustrating the example embodiments of the present disclosure, references to the drawings are made. It should be understood, however, that the application is not limited to the precise arrangements and instrumentalities shown. In the drawings.

DETAILED DESCRIPTION

A medical professional can correct an anatomical structure, such as a bone, for instance a mandible, using three-dimensional software to create a corrected bone image. A corrected anatomical image can refer to an image of any bone, such as a mandible, or other anatomical structure, such as soft tissue, that has a desired or repaired configuration. For instance, a corrected bone image may correspond to an image of a fractured bone that was manipulated to reduce the fracture and reconstruct the fractured bone. Similarly, the corrected bone image may refer to an image of a bone that has been surgically (for instance via an osteotomy) or otherwise altered to correct a genetic deformity. The bone of the corrected bone image can be any bone in the body of a human or other animal. In one embodiment, an image of the corrected bone can be received by an implant application, such as a bone implant application, which is a program, such as a software or hardware or combination of both, that can be run on any suitable computing device. The design of a bone implant can be fitted to the image of the corrected bone. The design of the bone implant can be repositioned to better fit the image of the corrected bone. A user can use the bone implant application to design a bone implant, for instance a bone plate that is fitted to the corrected bone, so as to be attachable to the corrected bone. While the illustrated embodiments are described herein with reference to a mandibular bone, it will be understood that the bone can be one of any number of other bones as desired. Further, it should be appreciated that the embodiments described herein can further be applied to the design of a soft tissue implant. In this regard, reference below to the bone implant application can be further construed as an anatomical implant application that can assist in the design of a bone implant, or can alternatively assist in the design of a soft tissue implant application.

The design of the bone implant can be fitted to the image of the corrected bone, so that a subsequent manufacture of a bone implant constructed in accordance with the bone implant image on the bone implant application will adequately conform to the corrected bone. For instance, manufacturing data that corresponds to the design of the bone implant can be received by a bone implant manufacturer, for instance a bone plate manufacturer. The manufacturer can fabricate a bone implant that corresponds to the bone implant image, which is a graphical depiction of the bone implant design. Thus, it can also be said that the fabrication of the bone implant is in accordance with the bone implant design. It will be appreciated that a bone implant can be fabricated from any biocompatible, implantable material as desired, including metals such as titanium, titanium alloy such as Ti-6Al-7Nb, or stainless steel, polymers such as polyetheretherketone (PEEK), reinforced plastics, and the like.

Figure 1:
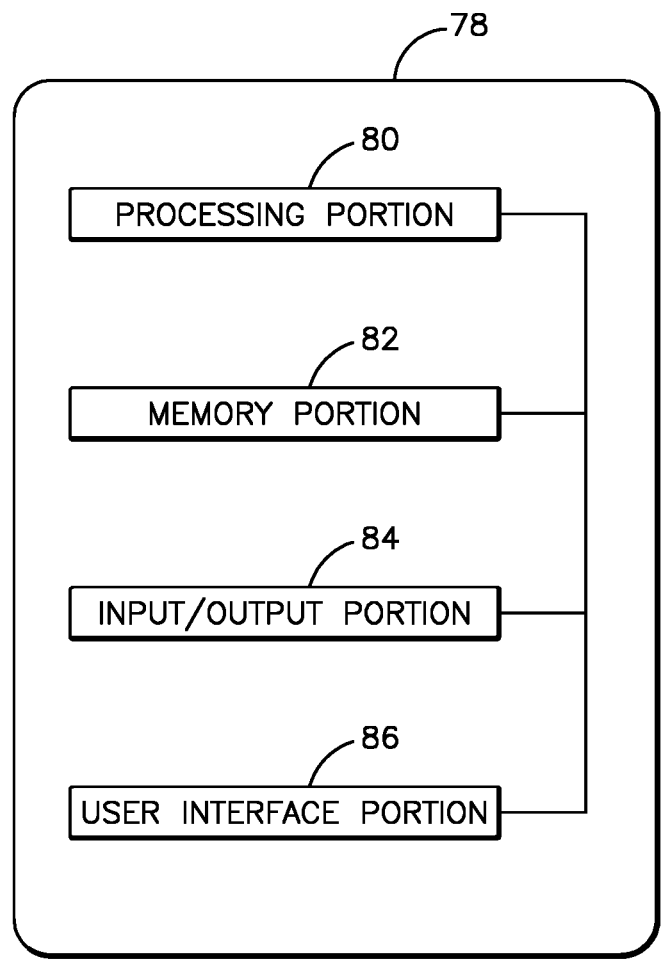
FIG. 1 is a block diagram of an example computing device for use in accordance with the present disclosure.

Referring to FIG. 1, any suitable computing device 78 may be configured to host the bone implant application. It will be understood that the computing device 78 can include any appropriate device, examples of which include a desktop computing device, a server computing device, or a portable computing device, such as a laptop, tablet or smart phone.

In an example configuration, the computing device 78 includes a processing portion 80, a memory portion 82, an input/output portion 84, and a user interface (UI) portion 86. It is emphasized that the block diagram depiction of computing device 78 is exemplary and not intended to imply a specific implementation and/or configuration. The processing portion 80, memory portion 82, input/output portion 84 and user interface portion 86 can be coupled together to allow communications therebetween. As should be appreciated, any of the above components may be distributed across one or more separate devices and/or locations.

In various embodiments, the input/output portion 84 includes a receiver of the computing device 78, a transmitter of the computing device 78, or a combination thereof. The input/output portion 84 is capable of receiving and/or providing information pertaining to communicate a network such as, for example, the Internet. As should be appreciated, transmit and receive functionality may also be provided by one or more devices external to the computing device 78.

Depending upon the exact configuration and type of processor, the memory portion 82 can be volatile (such as some types of RAM), non-volatile (such as ROM, flash memory, etc.), or a combination thereof. The computing device 78 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic disk storage or other magnetic storage devices, universal serial bus (USB) compatible memory, or any other medium which can be used to store information and which can be accessed by the computing device 78.

The computing device 78 also can contain the user interface portion 86 allowing a user to communicate with the computing device 78. The user interface 86 can include inputs that provide the ability to control the computing device 78, via, for example, buttons, soft keys, a mouse, voice actuated controls, a touch screen, movement of the computing device 78, visual cues (e.g., moving a hand in front of a camera on the computing device 78), or the like. The user interface portion 86 can provide outputs, including visual information (e.g., via a display), audio information (e.g., via speaker), mechanically (e.g., via a vibrating mechanism), or a combination thereof. In various configurations, the user interface portion 86 can include a display, a touch screen, a keyboard, a mouse, an accelerometer, a motion detector, a speaker, a microphone, a camera, a tilt sensor, or any combination thereof. The user interface portion 86 can further include any suitable device for inputting biometric information, such as, for example, fingerprint information, retinal information, voice information, and/or facial characteristic information. Thus, a computer system such as the computing device 78 can include a processor, a display coupled to the processor, and a memory in communication with the processor. The memory can have stored therein instructions that, upon execution by the processor, cause the computer system to perform operations, such as the operations described below. The display can be configured to display visual information, such as described with reference to FIGS. 4-27.

Figure 2:
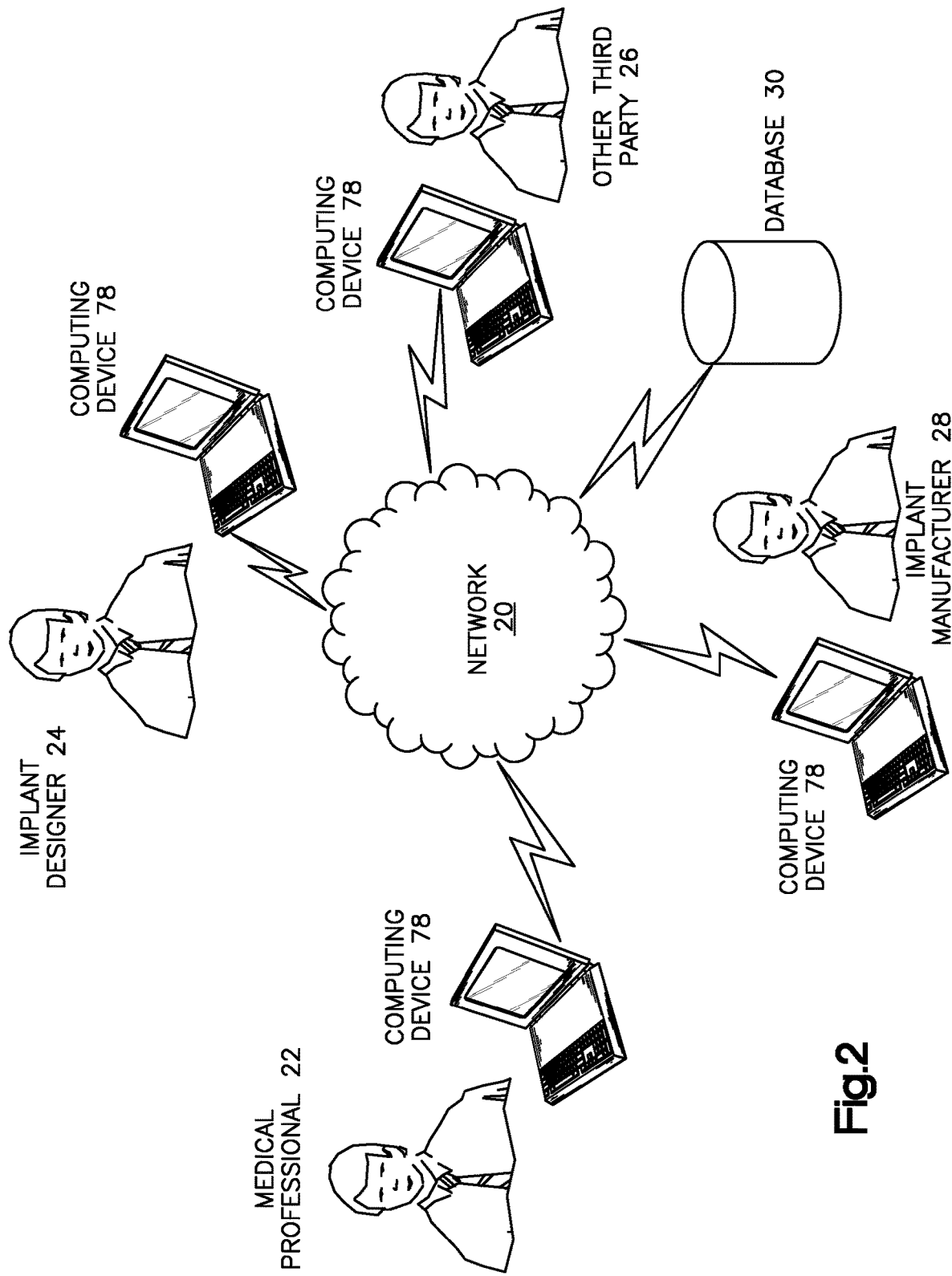
FIG. 2 is an example communication architecture for use in accordance with the present disclosure.

FIG. 2 depicts one example of a suitable communication architecture that can facilitate the design and the manufacture of a bone implant, it being appreciated that numerous suitable alternative communication architectures are envisioned. Once the bone implant application has been installed onto the computing device 78 such as described above or possibly another device, it can transfer information between other computing devices 78 on a common network 20, such as, for example, the Internet. In an example configuration, a medical professional 22 may transmit the corrected bone image to the computing device 78 of the implant designer 24 or another third party 26, such as another medical professional for example, via the network 20. Alternatively, the medical professional 22 or other party that creates the corrected bone image can also design the implant using the bone implant application. Thus, the corrected bone image and the bone implant application can be performed on the same computing device 78. After the bone implant is designed, it can be sent to the computing device 78 of a bone implant manufacturer 28.

The computing devices 78 and the database 30 depicted in FIG. 2 may be operated in whole or in part by, for example, a bone implant manufacturing company, a hospital, a healthcare professional, a bone implant design company, another third party, or by any combination of any of the above entities. As should be appreciated, each of the parties set forth above and/or other relevant parties may operate any number of respective computers and may communicate internally and externally using any number of networks including, for example, wide area networks (WAN's) such as the Internet or local area networks (LAN's). Database 30 may be used, for example, to store information regarding bones that are made available to the bone implant application. Database 30 may also be used, for example, to store information obtained from parties such as healthcare professionals and bone implant manufacturers.

Figure 3:
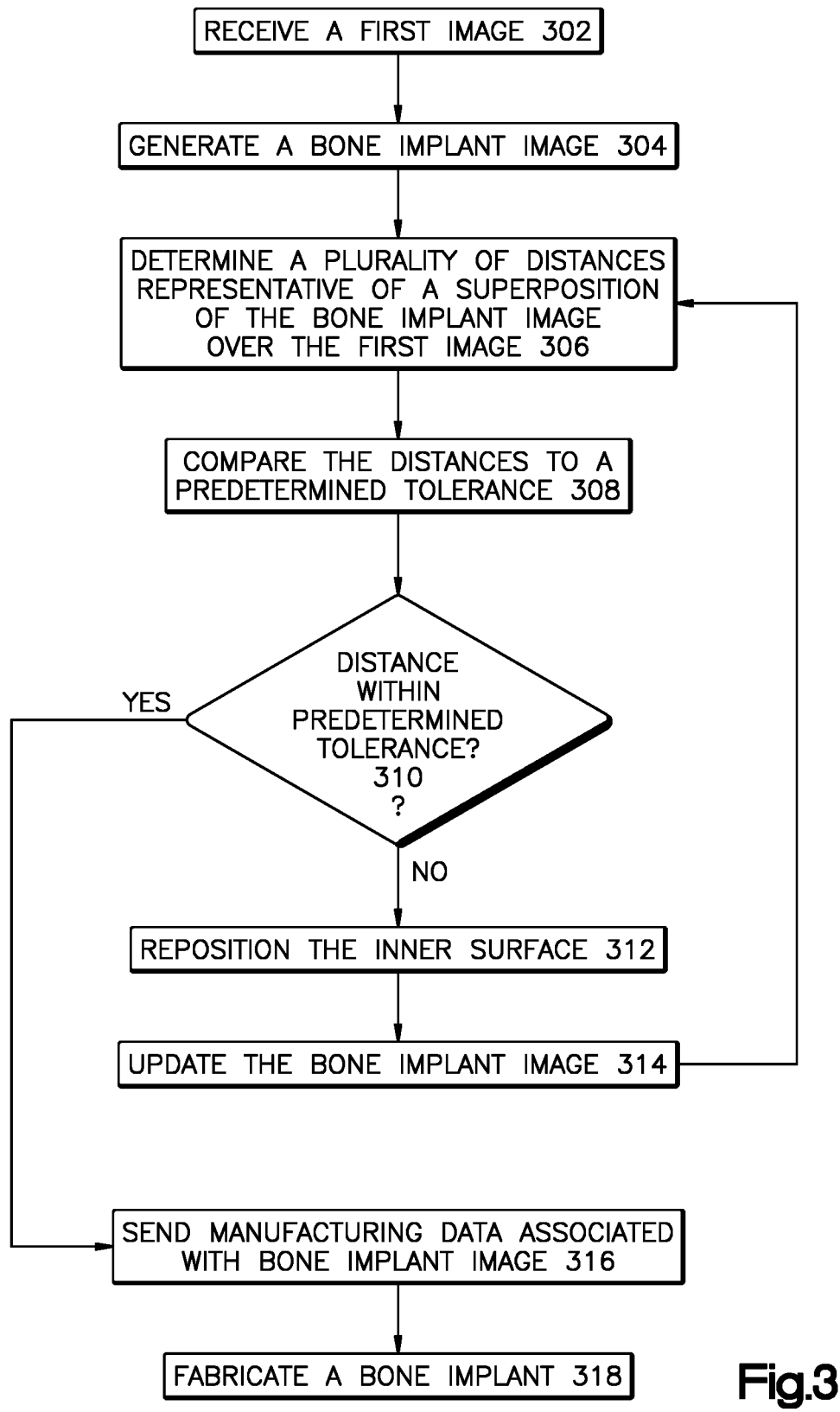
FIG. 3 is a flowchart of an example method for designing and manufacturing a bone implant.

Referring now to FIG. 3, the steps depicted in FIG. 3 can be performed by the bone implant application, which can be installed on a computing device such as a desktop, laptop, mobile phone, or tablet computer. Such software may communicate with one or more other computing devices via an architecture such as depicted in FIG. 2 and described above.

Figure 4:
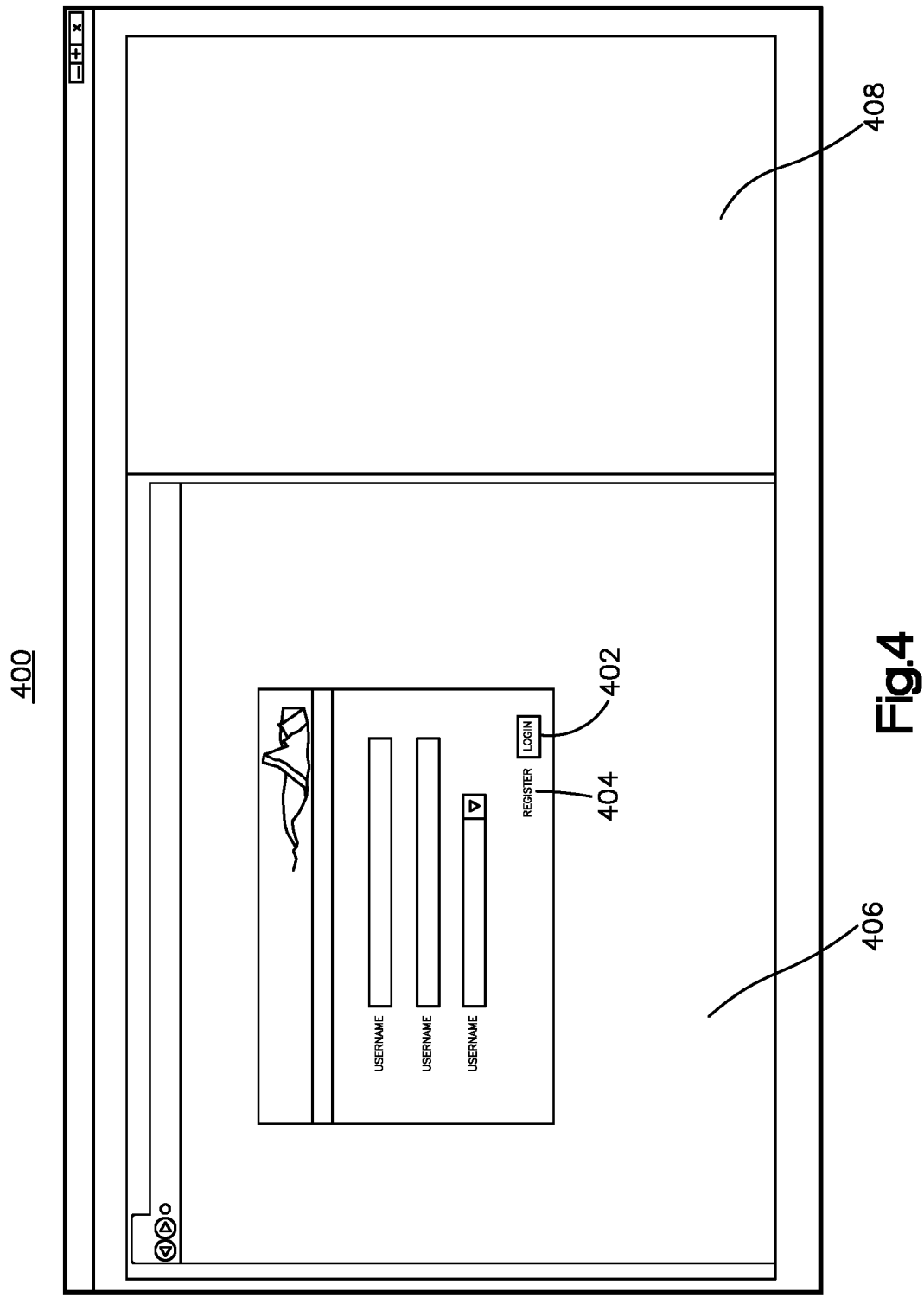
FIG. 4 is a screen shot depicting an example bone implant design application login page.

With continuing reference to FIG. 3, an anatomical image is received by the bone implant application at step 302. The anatomical image can be an image representative of any suitable anatomical structure as desired, such as a bone or soft tissue. The anatomical implant application can assist in the custom design of an implant that confirms to the anatomical structure. In instances where the anatomical image is a bone, the received bone image can be an image of any bone, as further described herein. Such an image may be received following a user login via a login page. Referring to FIG. 4, the login page 400 can be used to receive user identity information so that a user can receive access to the bone implant application. Example users include, without limitation, bone implant designers and healthcare professionals. User identity information may include, for example, a user name and password. Additionally, for example, biometric identity information such as a fingerprint or eye scan may be used if a user device is capable of obtaining such information. As shown in FIG. 4, if the user has previously registered with the bone implant application, then the user can enter his username and password to login via the login option 402. Once entered, this information may be submitted for verification. For instance, the entered username and password may be matched with a stored username and password. The bone implant application can further provide an indication of whether or not the user has been verified. If the verification has failed, the user may be prompted to re-enter the identity verification information or the user may be denied further access to the bone implant application. Further, the bone implant application can assign different levels of user rights to different users based, for instance, on the verification, and the user rights associated with the user. In one embodiment, the verified user may be granted access to read or view the bone implant image, but not edit, the bone implant image. In another embodiment, the verified user may be granted access to read or view the bone implant image, and additionally to edit the bone implant image.

Alternatively, if the user hasn't previously registered for instance, he can create a user account via the register option 404. After selecting the register option 404, the user can create an account by entering information such as his name and email and creating an associated username and password. The user may also indicate a preferred language such as, for example, English. Once entered, this information may be submitted for storage. As shown in FIG. 4, the login and register options 402 and 404, respectively, can be shown in a browser window 406 of the login page 400. The login page 400 can further include a three-dimensional (3-D) window 408. The 3D window 408 can be configured to display images that are created using, for example, any 3D-based application, such as Pro/Engineer (Pro/E) for instance.

Figure 5:
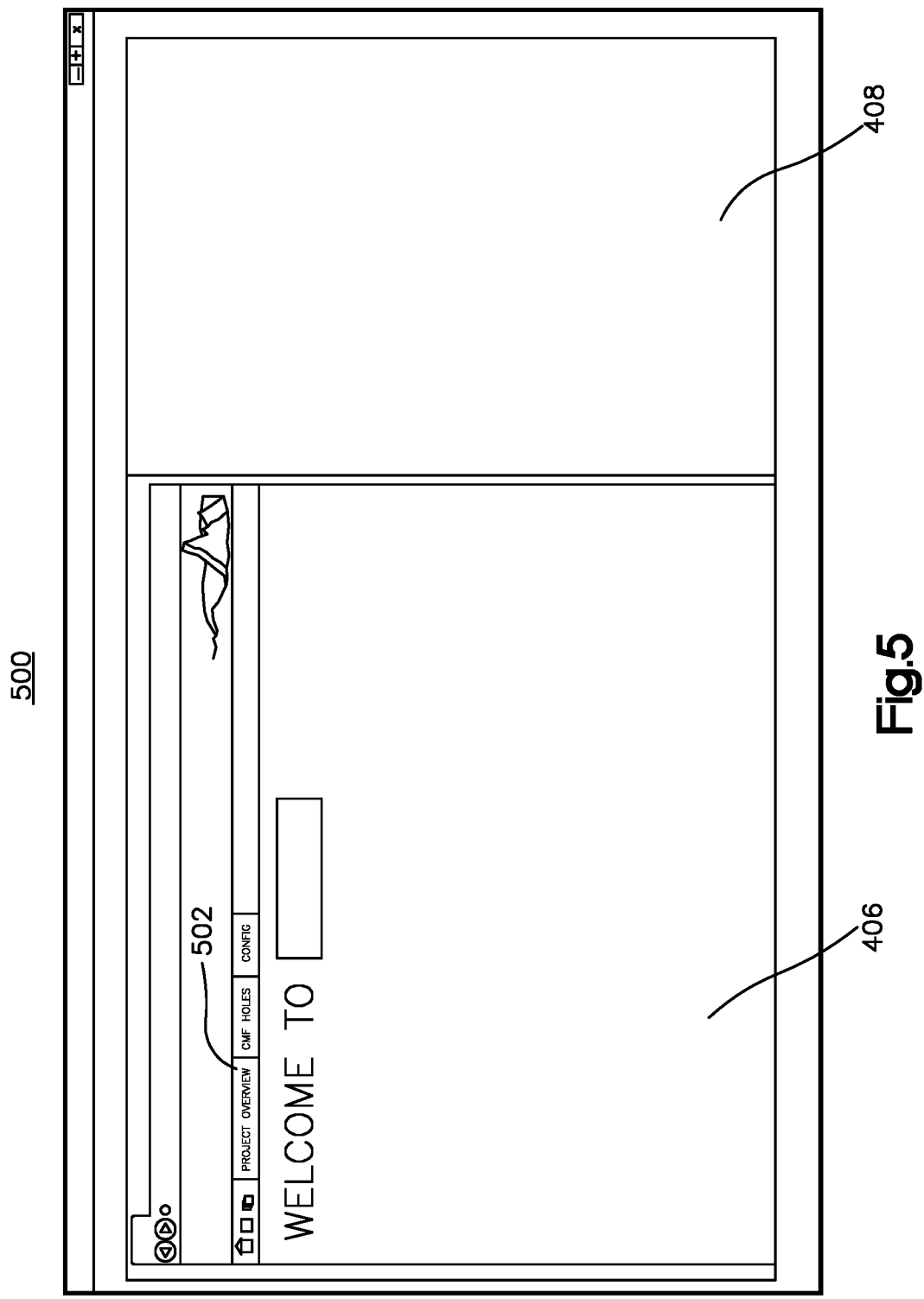
FIG. 5 is a screen shot of an example project page.
Figure 6:
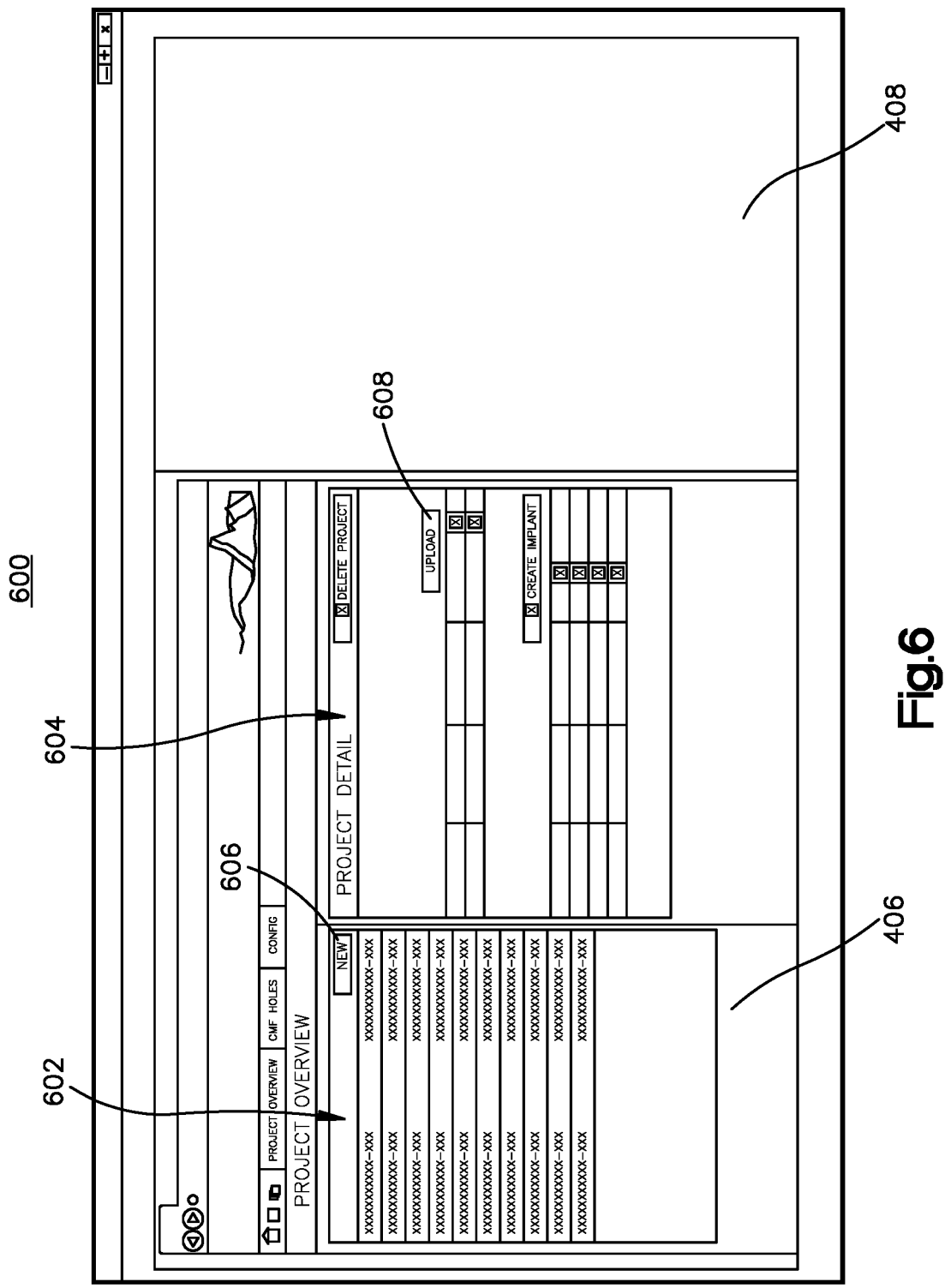
FIG. 6 is a screen shot of an example project detail page.

Referring to FIG. 5, once the user has been registered or a verification of the identity information has been received, a user can view projects via the project page 500. For instance, a project can include a file that stores a completed anatomical implant image design, such as a bone implant image design, a soft tissue implant image design, or the like, or an in-process anatomical bone implant image design, such as a bone implant image design, soft tissue implant image design, or alternative anatomical implant image design. In one embodiment, a user can select the project overview option 502 to view bone implant design projects that are saved in memory. Upon selecting the project overview option 502, a display of various projects can be rendered on a project detail page 600 shown in FIG. 6. As shown in the illustrated screen shot, the project detail page 600 can include a list of projects 602. The list of projects 602 can include a list of design projects that correspond to bone implant designs that have been started and/or completed. By selecting one of the projects in the project list 602, a user can view details of the selected project in a project detail window 604.

As shown in the illustrated screen shot, the project detail page includes the project detail window 604 in the browser window 406. As shown, details of the project that are displayed can include the project name, the patient's name, and the intended surgery date. Other details may relate to the project files such as the name and size and type of the files, the times at which various iterations of the files were saved. Other details may relate to implant instances such as the name of the instance and the status of the design. It will be appreciated that other details related to the bone, bone implant, patient, and/or project may be displayed on the project detail window 604 as desired. If the user wants to view and/or edit an existing project from the project list 602, the user can select a project from the list 602 and upload its corresponding data into the bone implant application by actuating an upload input 608, which can be a button or other suitable input. Alternatively, data can be previously uploaded into the bone implant application at step 302, and the input at the project list 602 causes the previously-uploaded data to be retrieved from memory. An existing project may be retrieved from local memory, such as from the memory portion 82 for instance, or from remote memory, such as from a remote database.

Figure 7:
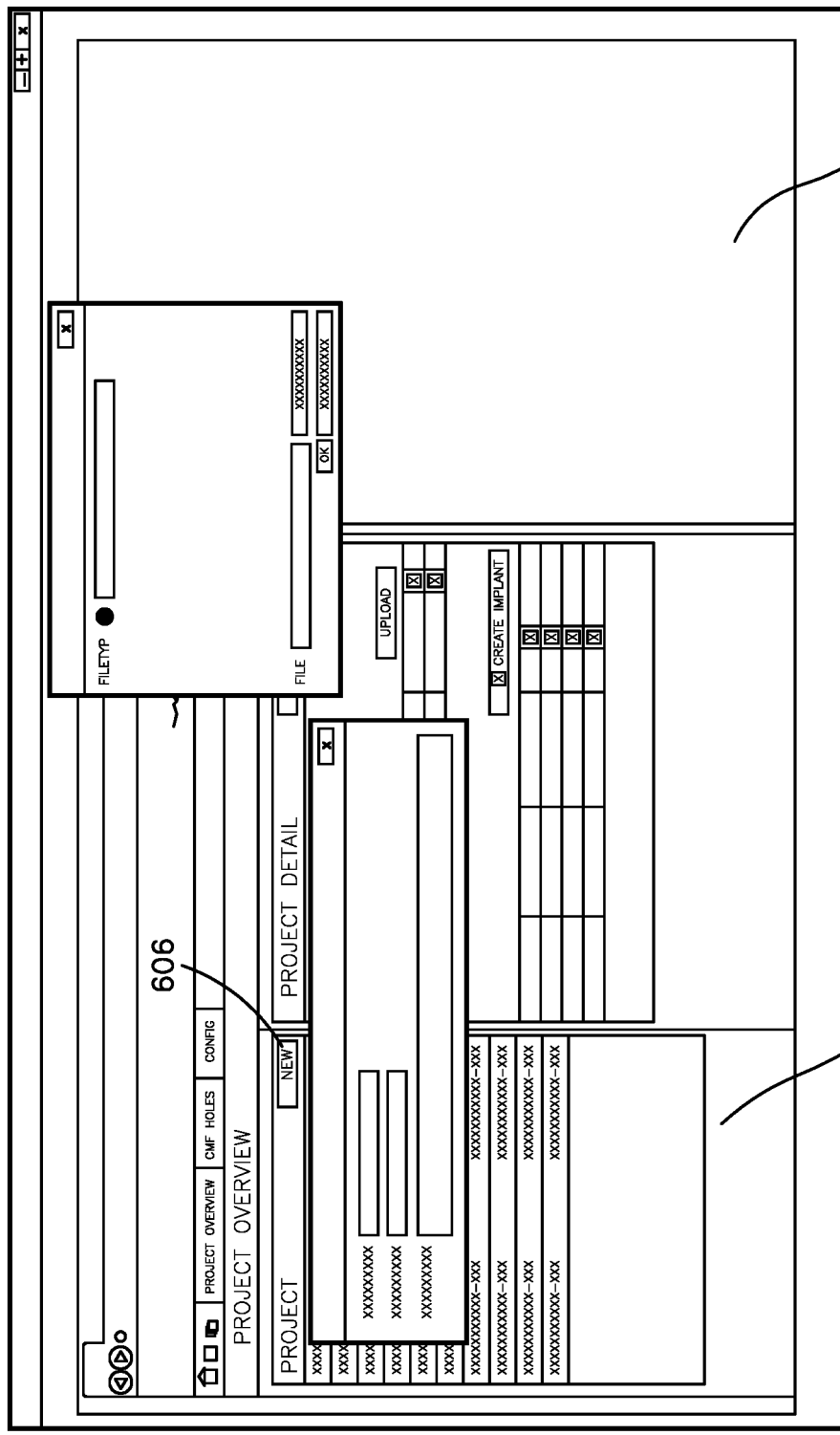
FIG. 7 is a screen shot of an example new project page.
Figure 8:
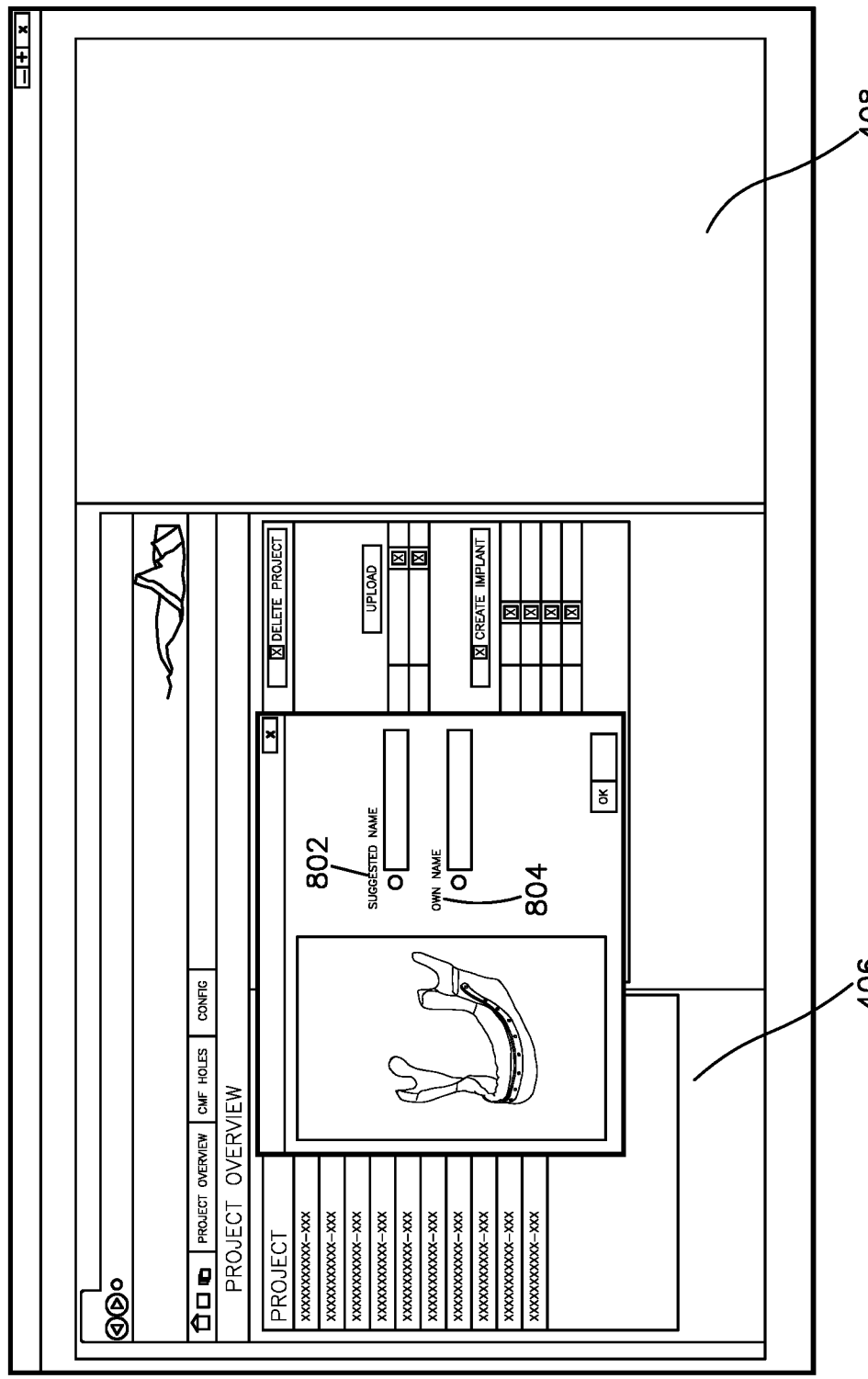
FIG. 8 is a screen shot of an example name page.

Alternatively, referring to the new project page 700 in FIG. 7, the user may create a new project by actuating a "new" input 606, which can be a button or other suitable input. The user may be prompted to enter project information such as the patient's name, the date of surgery, or the like. Upon creating a new instance of an existing bone implant design project, the user can name the instance via the name page 800 shown in FIG. 8. A suggested instance name 802 may be displayed. A user may choose to name the new instance according to the suggested instance name 802. Alternatively, a user may create an instance name via the own name option 804.

Figure 9:
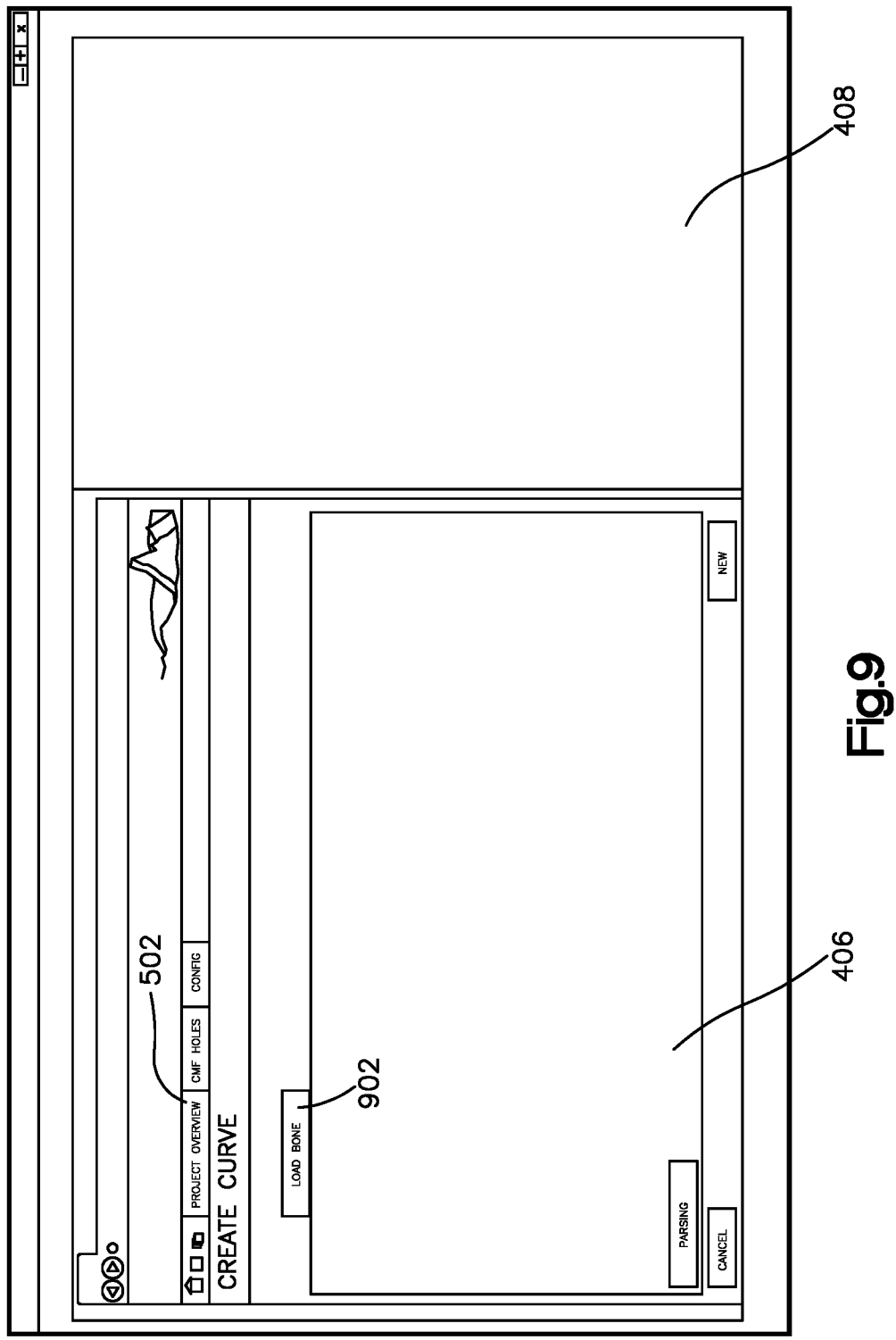
FIG. 9 is a screen shot of an example load bone page.
Figure 10:
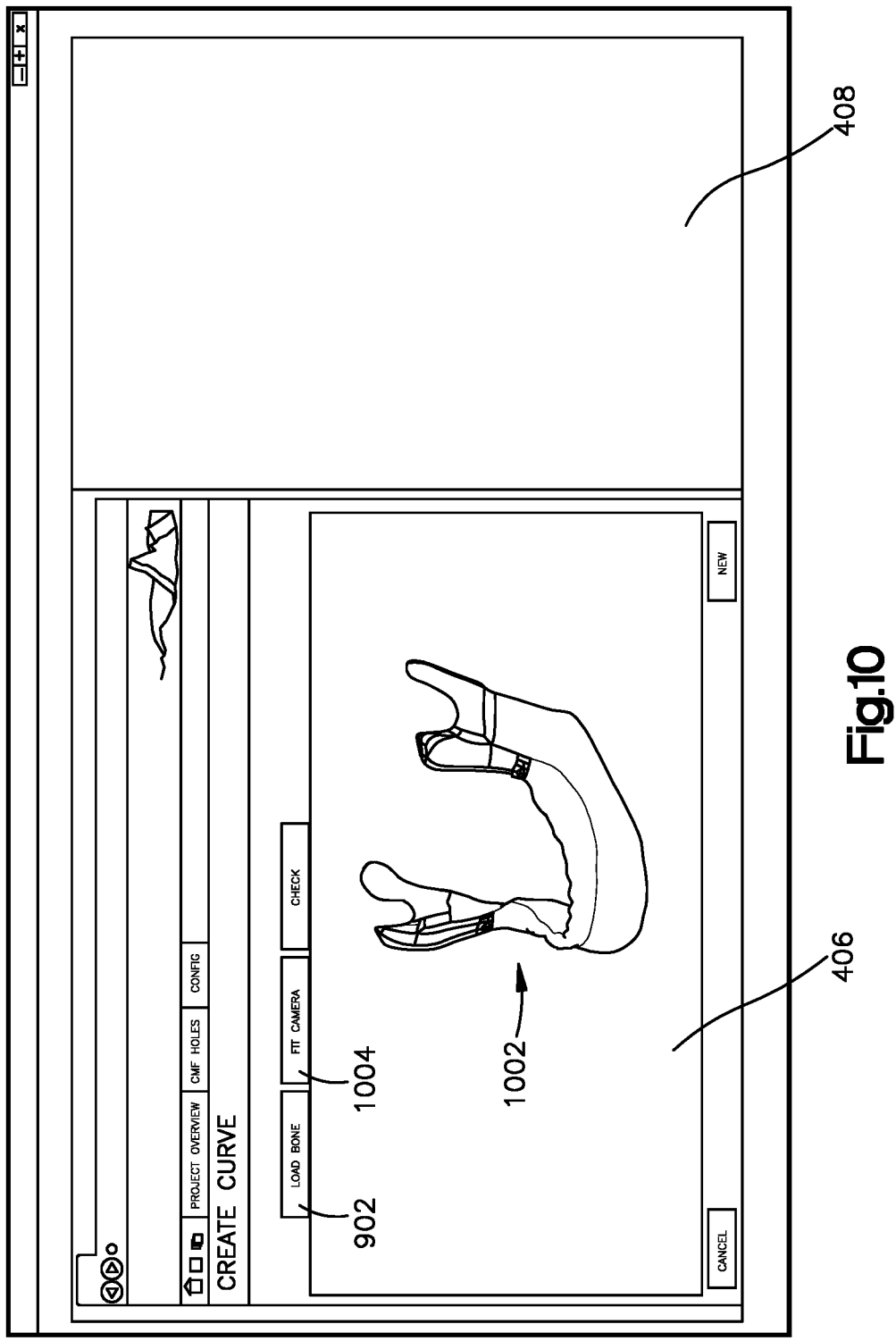
FIG. 10 is a screen shot of an example bone display page with an image of a corrected bone.

Referring to FIG. 9, a user can load a corrected bone image from the load bone page 900. For instance, a user can actuate a load bone input 902, which can be a button or other suitable input, to upload the desired bone image to the bone implant application. It will be understood that actuation of the load bone input 902 can cause a bone image to be retrieved and forwarded to the computing device 78 as shown in FIG. 1. For instance, a corrected bone image can be created by a medical professional and can be retrieved from local memory (e.g., of the computing device 78) or from another local or remote computing device.

Figure 13:
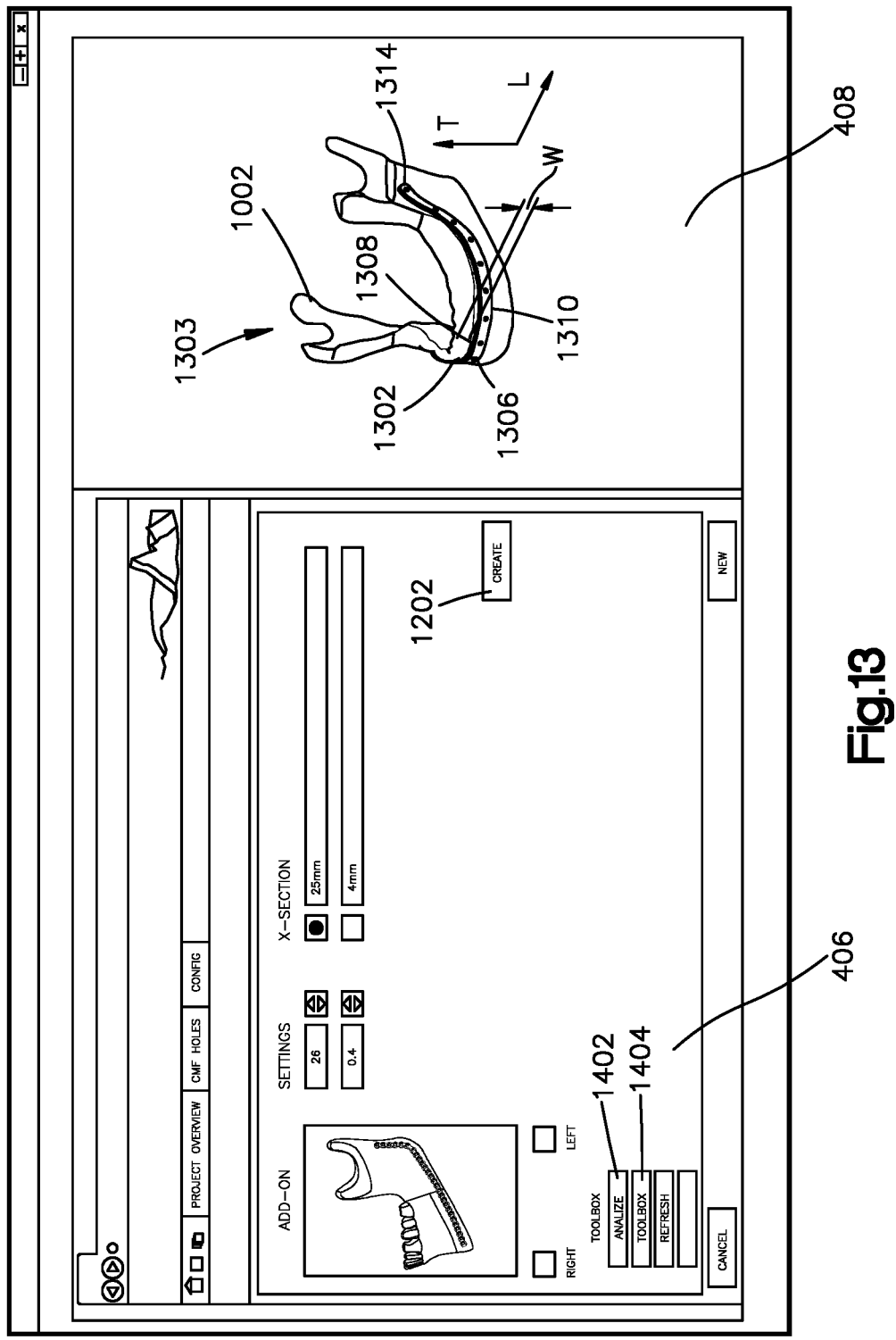
FIG. 13 is a screen shot of a bone implant image page.
Figure 14:
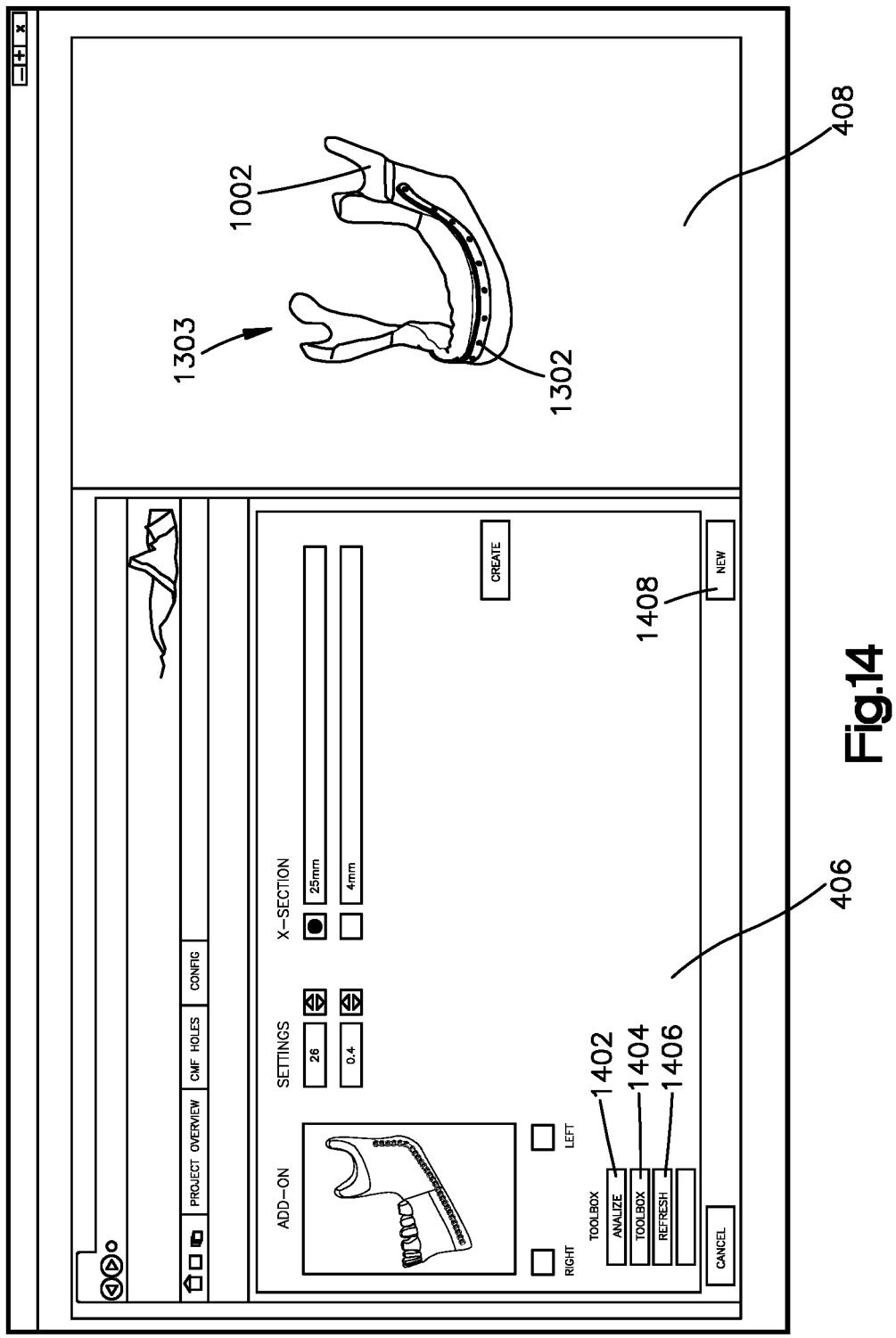
FIG. 14 is a screen shot of a smooth curve option.

Referring again to FIG. 3, an anatomical implant image can be a bone implant image 1302 as illustrated at FIG. 13, or any suitable alternative anatomical implant image such as a soft tissue implant image, can begin to be generated at step 304. The anatomical implant image can be associated with a corresponding anatomy that is represented by a corrected anatomical image. For instance, when the anatomical implant image is the bone implant image 1302, the bone implant image 1302 can be associated with a corresponding bone that is represented by a corrected bone image, such as the bone image 1002 shown in FIG. 10. Alternatively, when the anatomical implant image is a soft tissue implant image, the soft tissue implant image can be associated with a corresponding soft tissue that is represented by a corrected soft tissue image. A user can manipulate the anatomical image, such as the bone image 1002, as desired. For instance, a user can fit the bone image 1002 into the browser window 406 by actuating an input 1004, which can be a button or any other suitable input. A user can also actuate a user input, such as a mouse for instance, to change the view of the bone image. By way of example, and without limitation, a user can actuate a mouse or keys to rotate the bone image about various axes that the use selects, zoom in or out on the bone image, or view the bone image from other perspectives.

Figure 11A:
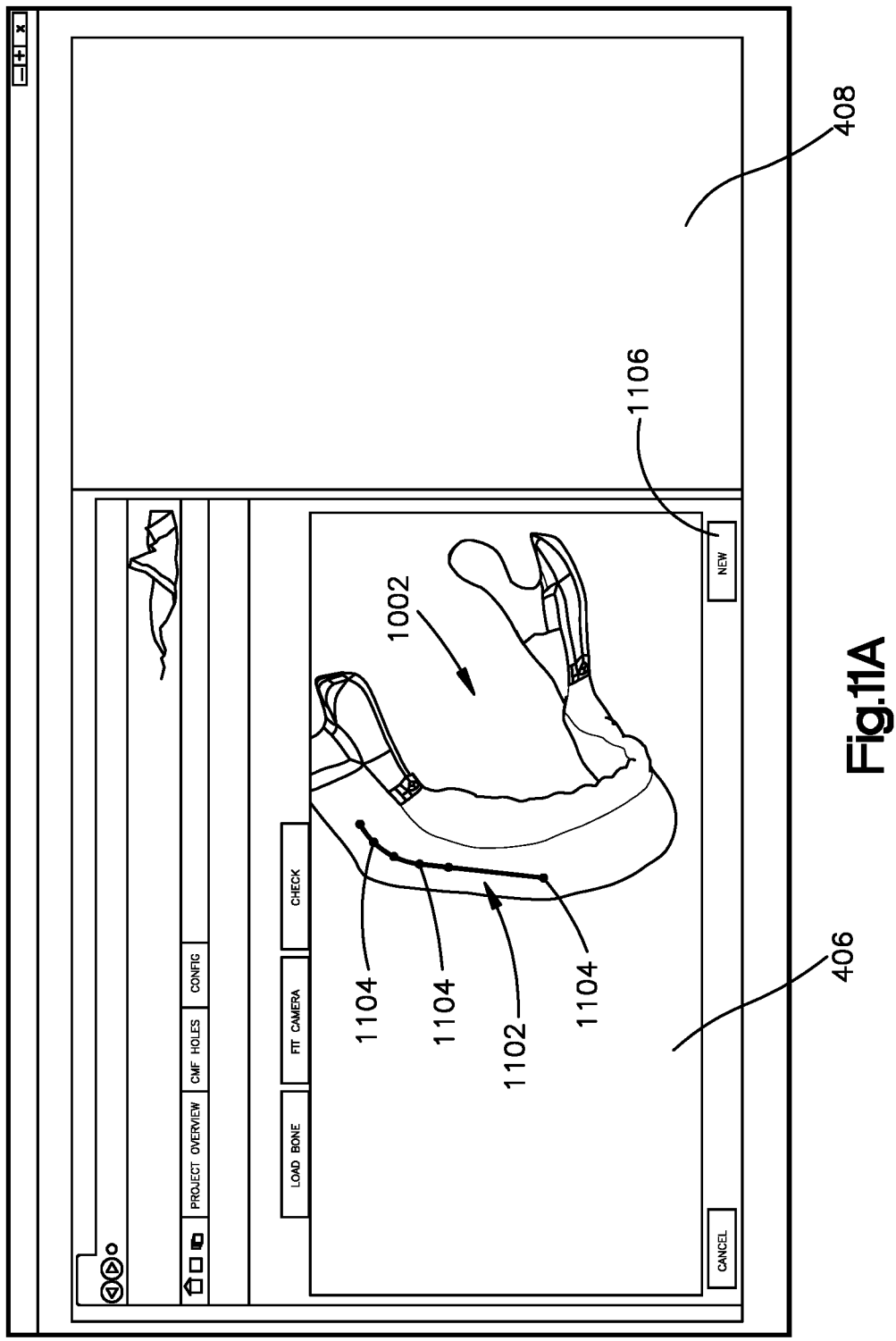
FIG. 11A-B are screen shots of example create curve pages with a curve draw on the bone image from FIG. 10.
Figure 11B:
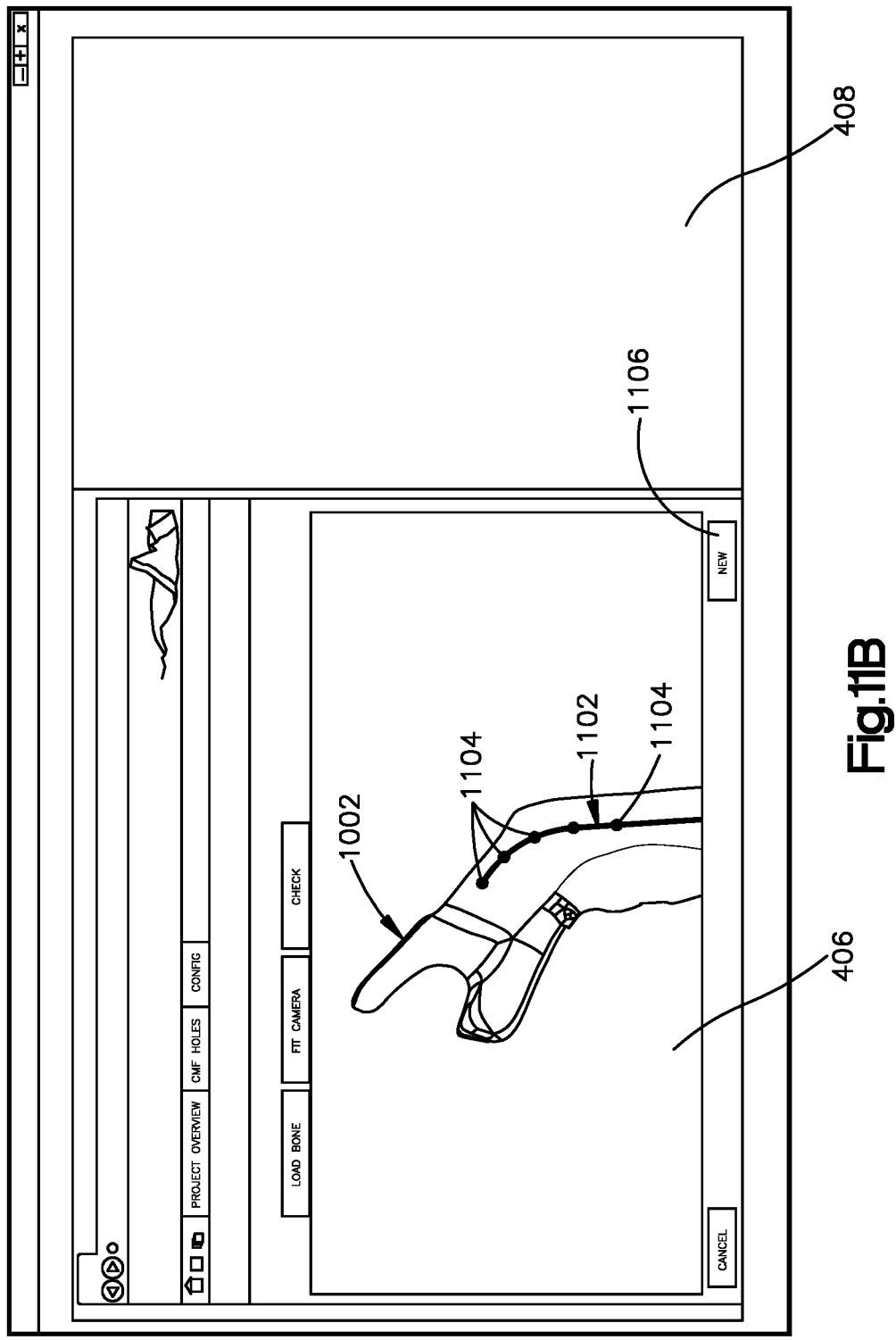

Referring to FIGS. 11A-B, a bone implant image can be generated at step 304. For instance, step 304 can include drawing a curve line, which can be a segmented line 1102 that represents and substantially defines a central path along which the bone implant image will follow. For instance, a user can click a mouse to create a series of points 1104 that are spaced from each other along the path. The implant application can connect points 1104 with a line to create a line 1102. The line can be straight as illustrated, or can alternatively be curved as desired. Thus, each line between two points can define a segment of the segmented line 1102. Because each segment can define a change in direction, the segmented line 1102 can create a central axis of elongation of the bone implant image 1302. For instance, the bone implant application can create the bone implant profile along the segmented line 1102. As shown, the segmented line 1102 can also generally define the length of the bone implant. In an example embodiment, a user can "undo" one or more segments up to all segments of the segmented line 1102 by selecting the load bone input 902. Such a selection may allow a user to draw a new segmented line on the bone. Alternatively, a user may select the next input 1106, which can be a button or other input, when the segmented line 1102 is satisfactory to the user.

Figure 12:
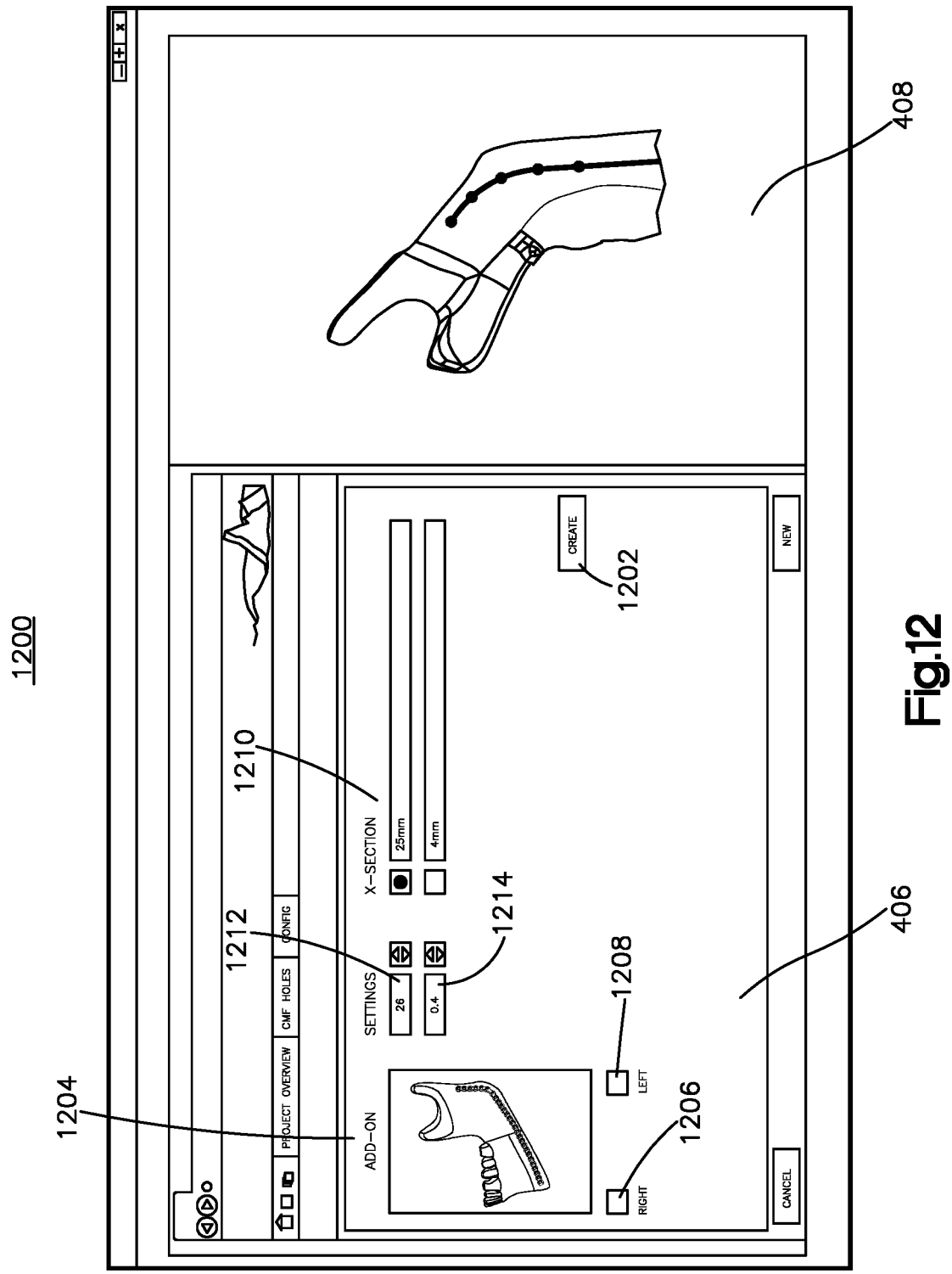
FIG. 12 is a screen shot of an example bone implant detail page.

Referring to FIG. 12, a bone implant detail page 1200 in FIG. 12, other parameters of a bone implant can be selected by the user. For instance, a user may select whether a condylar head 1204 is to be included in the bone implant image 1302. If such a condylar head 1294 is desired, the user can select the side of the cranium to which the condylar head 1204 is configured to attach via the right and left inputs 1206 and 1208, respectively, which can be buttons or other inputs. Although the illustrated embodiments depict the bone implant application in connection with the design of a mandibular bone plate, it should be appreciated that the bone implant application can be configured to design other bone implants that repair or correct other bones, for instance the cranium, eye socket, or nasal bones, long bones, or the like.

Still referring to FIG. 12, a user may select a bone implant type 1210. As illustrated, the bone implant type refers to the thickness of the cross section of the bone implant, but create page 1200 can be constructed so that the bone implant type refers to any other selectable bone implant parameters or characteristics as desired. The create page 1200 may also allow the user to select an offset 1212 between slices 1604 (see FIG. 16). The offset 1212 can define a distance along the path of elongation of the bone implant image 1302 (see FIG. 13). As described further below with reference to FIG. 16, the offset between slices 1604 may refer to the distance along the segmented line 1102 between fittings, or virtual "slices" of the bone implant. Alternatively, the user can select a number of slices 1604, and the bone implant application can place the slices 1604 along the segmented line 1102 in which each successive slice is substantially an equal distance along the segmented line 1102 from the previous slice. In yet another embodiment, the number of slices and location of the slices along the segmented line 1102 can be determined by the bone implant application, for instance based on the bone image and/or or the type of bone implant. The create page 1200 may display suggested offsets between slices for the user to select.

Similarly, a user can select a bone offset 1214 on the create page 1200. Alternatively, the bone offset may be stored in memory and/or suggested to a user. As described further below, the bone offset 1214 can refer to a distance between an inner surface of the bone implant and an aligned outer surface of the bone to which the inner surface of the bone implant faces at each slice. For instance, if the bone offset 1214 is too small at one or more slices 1604, the bone plate image may interfere with the bone image at the one or more slices 1604 when the bone implant is positioned adjacent the bone in a manner consistent with attaching the manufactured bone implant to the corrected bone. The create page 1200 can display a bone offset tolerance that is stored in memory and/or suggested to a user. As described further herein, the bone offset tolerance may refer to a range of acceptable distances as measured between the inner surface of the bone implant and the outer surface of the bone that is aligned with the inner surface of the image to which the bone implant is fitted. For instance, a bone offset 1214 that is less than the bone offset tolerance may create interference between the bone implant and the bone. In an example embodiment, the tolerance can be selected by the user, and tolerance may be provided to a user by the bone implant application. The recommended bone offset tolerance can be based on the bone that is being corrected and the bone implant that is being fitted to the bone. For instance, the bone offset tolerance may depend on the type and/or size of the bone implant, and can vary along the length of the implant image. Thus, the bone offset tolerance of one slice 1604 can be different than the bone offset tolerance of another slice 1604. The create page further includes a create input 1202 that can be selected by the user to create an implant sweep, as will now be described.

In particular, referring to FIGS. 13 to 16, the creation of an implant sweep can result in the generation of the bone implant image 1302 (which was generated at step 304 of FIG. 3) that is to be fitted to the bone that is represented by the bone image 1002. Thus, the bone implant image 1302 that is associated with an anatomical structure can be generated by the bone implant application. The bone implant application can displace a superimposition 1303 of the bone implant image 1302 over the bone image 1002. The bone implant image 1302 can define an outer surface 1306 and an inner surface 1304 that is opposite the outer surface 1306 and faces the bone image 1002. The inner surface 1304 can face the bone image 1002. It should thus be appreciated that a distance between the inner surface 1304 and the outer surface 1306 define a thickness of the bone implant image 1302. The bone implant image 1302 can further define a top end 1308 and a bottom end 1310 spaced apart from the top end 1308 along a transverse direction T so as to define a width W of the bone implant image 1302. Referring to FIG.

16, the bone implant image 1302 can define opposed ends 1312 and 1314 that define a length L of the bone implant image 1302.

With continuing reference to FIG. 13, the bone implant application can include an analyze surface input 1402 that may be selected to cause the bone implant application to analyze the machinability of a bone implant that is represented by the bone implant image 1302. For instance, a machinability analysis may include identifying a plurality of cutting instruments. The identified cutting instruments can be pre-loaded into the bone implant application, or selected by the user or bone implant manufacturer. Examples of cutting instruments can include a profile cutter and a row cutter. The bone implant application can determine whether either or both of the plurality of cutting instruments are capable of producing a bone implant in accordance with the bone implant image 1302. For instance, one or more regions of the bone implant may be identified and the bone implant application can determine whether each of the identified cutting instruments are capable of producing each of the regions in accordance with the bone image. If a region is capable of being produced with at least one of the cutting instruments, one of the cutting instruments can be selected for each region. For instance, cutting instruments can be selected based on a predetermined hierarchy. Such a hierarchy can correspond to preferences and/or capabilities of a particular medical professional, designer, manufacturer and/or other party. Alternatively, a user can select one of the plurality of cutting instruments. In accordance with the illustrated embodiment, a graphical indication can be generated that indicates which cutting instrument corresponds, for instance is selected for fabricating, to each of the one or more regions of the bone implant image 1302. By way of example, the graphic indication of each bone implant region may include 1) a first color when a row-cutter can create the region, a 2) a second color when a profile cutter can create the region, and 3) a third color when none of the available cutting instruments can create the region from a stock of raw material.

The bone implant application allows the user to alter the bone implant image 1302 when the bone implant application identifies one or more regions of the bone implant image that is not manufacturable using one of the plurality of bone cutting instruments. In particular, referring to FIG. 14, the bone implant image 1302 can be altered by selecting a smooth curve input 1404, which can be a button or other input. This option will smooth the segmented line 1102 depicted in FIGS. 11A and 11B and is representative of the curve along the length of the bone implant image 1302. In an example embodiment, the segmented line 1102 can be automatically smoothed during the machinability analysis. In yet another example, a user can manually smooth the segmented line 1102, such as by drawing a new segmented line 1102, which can include additional segments so as to more precisely control the curvature of the bone implant image along the segmented line 1102. It should be appreciated that the user can further remove one or more points 1104 of the segmented line 1102. Such an alteration may change the machinability analysis. Subsequent actuation of the smooth curve input 1402 can adjust a geometric configuration, such as a curvature, of the one or more regions, for instance at the points 1104, so that at least one of the plurality of cutting instruments can create the one or more regions of a bone implant corresponding to the adjusted bone implant image that were previously identified as not machinable using the plurality of cutting instruments. After the curve of the bone image is smoothed, a user may create an updated bone implant image 1302 (see FIG. 14) by actuating the refresh implant input 1406, which can be a button or other input. It will be understood that a curve can be smoothed and a bone implant can be refreshed as many times as desired. The bone implant application can allow the user to adjust the fit of the bone implant image to the bone image by selecting the next input 1408, which can be a button or other input, is actuated.

Figure 16:
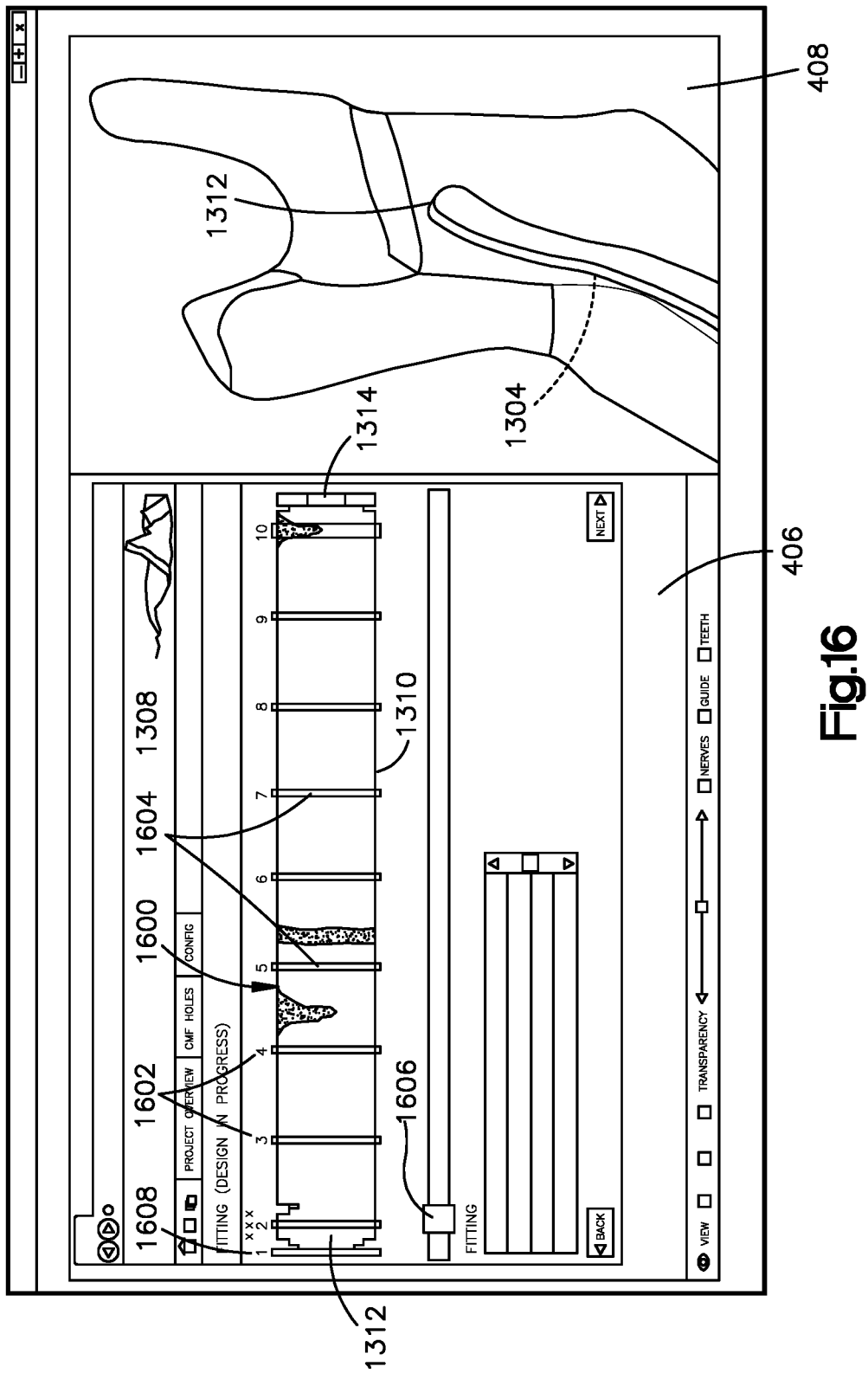
FIGS. 16-21 are screen shots of example fitting pages including a plan view of a bone implant image.

For instance, referring to FIGS. 16-21, various displays may enable the bone implant image 1302 to be fitted to the bone image 1002. With additional reference to FIG. 3, at 306, a plurality of distances can be determined as measured from aligned locations of the inner surface 1304 of the bone implant image 1302 to the outer surface of the bone image 1002 in respective straight lines such that the distances are representative of the superimposition 1303. Thus, the plurality of distances can be measured from respective locations of the inner surface 1304 to the bone image 1002, wherein the distances are representative of a the superimposition 1303 of the implant image 1302 over the bone image 1002. With particular reference to FIG. 16, the distances can be determined by sweeping along the bone implant image 1302 between slice locations 1602 along a width W of the bone implant image 1302. The slice locations 1602 can represent points along a length L of the bone implant image 1302 that correspond to the slices 1604. The bone implant application can characterize the fit of the bone implant image 1302 to the bone image 1002 along each of the slices 1604 at the slice locations 1602 when the bone implant image 1302 is superimposed over the bone image 1002. For instance, the bone implant application can compare the bone offset at each of the slices 1604 to the stored tolerance. A slice 1604 that is fitted to the bone can extend along a substantial entirety of the width W of the bone implant image 1302. Sweeping may refer to measuring distances at a plurality of locations between slice locations 1602, and thus between slices 1604, wherein the distances can be measured from the inner surface 1304 to the bone image 1002. A slice 1604 can extend from the top end 1308 to the bottom end 1310. Distances can also be measured at any number of locations between each slice 1604 including, for example, at any number of locations throughout the entire length L and width W of the bone implant image 1302 or only at selected locations.

In accordance with the illustrated embodiment in FIG. 16, the slice locations 1602 can be spaced apart an equal distance, or variable distances, from each other along the length L of the bone implant image 1302. Further, each of the slices 1604 can have a respective orientation that can vary as desired. For instance, the orientation can be perpendicular to the top and bottom ends 1308 and 1310, or define any angle with respect to the top and bottom ends 1308 and 1310 as desired. Thus, while the slices 1604 are elongate along the width W of the bone implant image 1302 in accordance with the illustrated embodiment, it will be understood that the orientation of the slices can vary as desired, for instance the slices can be angled with respect to the width W or the slices can be elongate long the length L of the cable. In example embodiment, the number of slice locations 1602 can based on, for instance equal to, the user-selected offset number that can be received via the bone implant detail page 1200.

Figure 15:
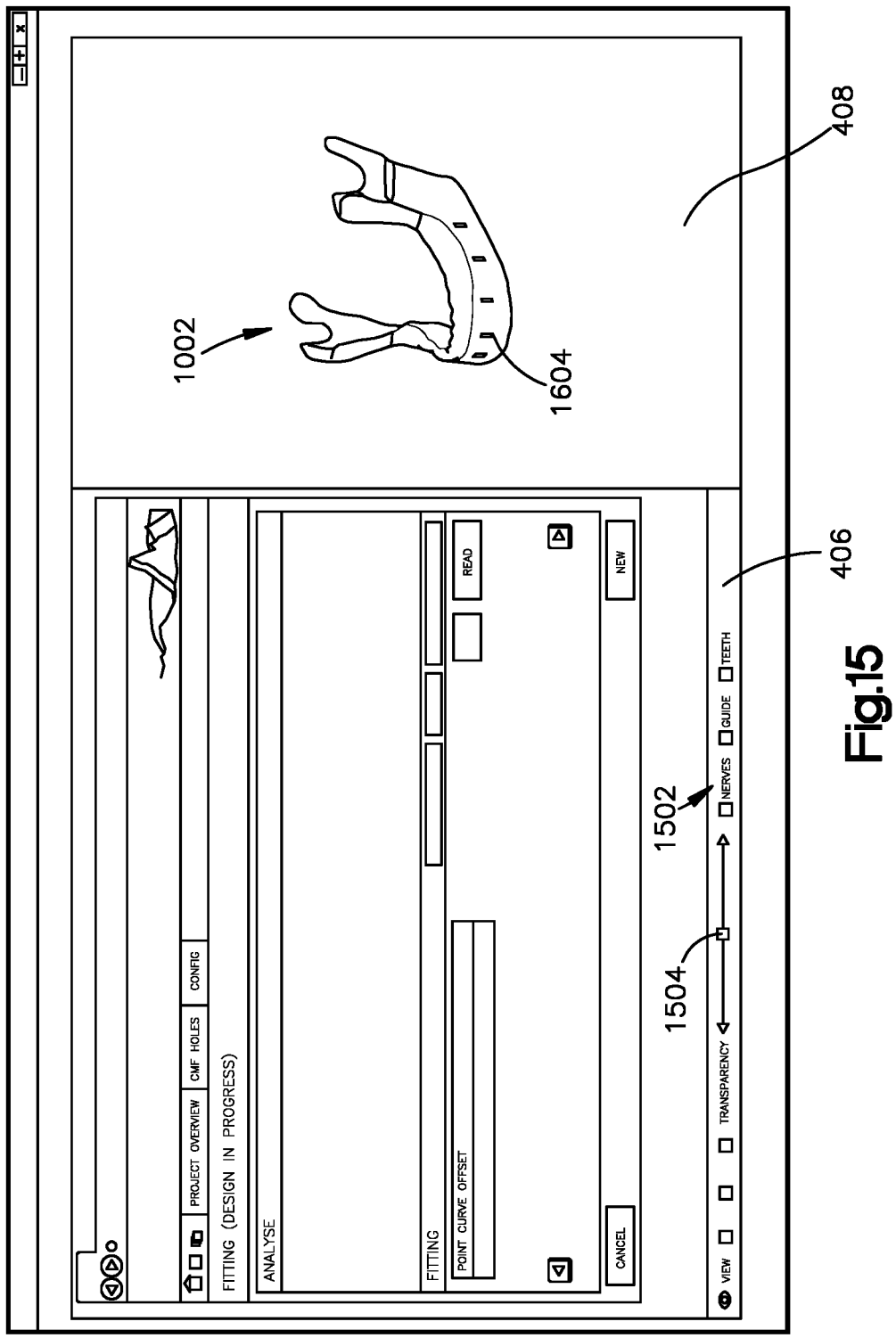
FIG. 15 is a screen shot of a transparency toolbar.

Referring to FIG. 15, the bone implant application can display a transparency tool bar 1502 that can be actuated by the user so as to select various regions of the bone implant image 1302 and the bone image 1002 transparent. Thus, the user can actuate the transparency tool bar 1502 to control what viewable features are displayed in the 3D window 408. In accordance with the illustrated embodiment in FIG. 15, the bone image 1002 is displayed with the slices 1604 superimposed on the bone image 1002. Thus, the portions of the bone implant image 1302 can be transparent as output by the bone implant application. In accordance with the illustrated embodiment, a user may decide to view or make transparent various features such as images of teeth, nerves, guiding points, and bones, as well as some or all of the bone implant image 1302. It will be understood that any features may be available for selection on the transparency tool bar 1502 as desired. It will further be understood that features that are available for viewing in the 3D window 408 may depend on the type of bone and/or the type of bone implant. For instance, teeth may be available for viewing in a bone image of the mandible bone, but may not be available for viewing in a bone image of various other bones. In accordance with the illustrated embodiment, the transparency tool bar 1502 may include a transparency cursor 1504. For instance, sliding the transparency cursor 1504 in a first direction may render a selected feature more transparent in the 3-D window 408, and sliding the transparency cursor 1504 in a second direction opposite the first direction may render a selected feature less transparent in the 3-D window 408. Thus, a user may be able to focus on a particular feature while viewing other features.

Referring again to FIGS. 16 to 21, the bone implant application can display a fitting matrix 1600 in the browser window 406. The fitting matrix 1600 may correspond to the superimposition 1303 displayed in the 3-D window 408 of FIG. 16. For example, a user can move a cursor on a location of the fitting matrix 1600 to view the corresponding location on the superimposition 1303. Further, a distance value 1608 may be displayed as part of the fitting matrix 1600 that corresponds to a desired location of the bone implant image 1302 or alternative anatomical implant image, which can be indicated by the location of the cursor. The distance value 1608 may represent the distance between the inner surface 1304 and the aligned bone image 1002 at the location on the bone implant image 1302 that corresponds to the location of the cursor. As shown in the illustrated embodiment, the value 1608 is displayed in millimeters, although it will be understood that the value 1608 can be displayed in any unit of measurement as desired.

It should be appreciated that the distances, and thus the values 1608, can represent whether the bone implant image 1302 is properly fit to the bone image 1002 in the superimposition 1303. If the value 1608 is higher than a predetermined value at a given location, the bone implant application can provide an output that indicates that the bone implant image 1302 is spaced farther from the bone image 1002 than desired at that location. If the value is less than a predetermined value (or is a negative number) at a given location, the bone implant application can provide an output that indicates that the bone implant 1302 is spaced closer to the bone image 1002 than desired at that location, or in fact indicates that the bone implant constructed in accordance with the bone implant image 1302 would interfere at that location with a bone that is represented by the bone image 1002.

Thus, at step 308 of FIG. 3, the distances that are representative of the superimposition 1303 of the bone implant image 1302 over the bone image 1002 can be compared to the bone offset tolerance. The fitting matrix 1600 can represent a graphical representation of the comparison. Thus, the bone implant application can generate a graphical indication, for instance in the fitting matrix 1600, of the comparison of the distances to the predetermined tolerance. For instance, the predetermined tolerance may define a low threshold and a high threshold, and the graphical indication may include a first color or other graphical representation when a distance is greater than the high threshold of the bone offset tolerance, a second color or other graphical representation (different from the first color or other graphical representation) when a distance is less than the low threshold of the bone offset tolerance, and a third color or other graphical representation (different from the first and second colors or other graphical representations) when the distance is between the low and high thresholds of the bone offset tolerance. It should be appreciated that various locations along each slice 1604 can be identified having different spatial relationships with respect to the bone image 1002. For instance, one location along a given slice 1604 can be identified as spaced too far from the bone image 1002, while another location along the given slice 1604 can be identified as spaced to close to (or interfering with) the bone image 1002. The fitting matrix 1600 may further include a summary bar 1606. The summary bar 1606 may provide a visual indication of the average distance along the width W at a respective slice location 1602. Thus, the user may be able to inspect the regions of the bone implant that may interfere with the bone and regions of the bone implant that may be too far away from the bone.

At step 310 of FIG. 3, it is determined whether one or more distances are not within the bone offset tolerance. If any distances, for instance at least a select one of the plurality of distances, are not within the bone offset tolerance ("NO" branch of step 310), then the inner surface 1304 of the bone implant image 1302 may be repositioned so as to change the at least select one of the plurality of distances (step 312). Referring to FIG. 3, after repositioning, the process may return to step 306 where the plurality of distances are determined in the manner described above. The bone implant application can allow the bone implant image 1302 to be repositioned in a number of different ways. For instance, in one embodiment, the bone implant application may automatically reposition the inner surface 1304 in response to a distance being outside of a predetermined tolerance. For instance, a region on the bone implant image 1302 that is identified as being spaced too far from the bone image 1002 can be repositioned closer to the bone image 1002. Furthermore, a region on the bone implant image 1302 that is identified as being spaced too close to (or interfering with) the bone image 1002 can be repositioned farther from the bone image 1002.

In another example embodiment, repositioning may occur in a response to a user command. Repositioning the inner surface 1304 may include moving at least a portion of the inner surface 1304 (for instance both the top and bottom ends 1308 and 1310) away from the bone image 1002 so as to increase at least one of the plurality of distances, for instance when at least one of the distances is a negative number and/or less at least one of the distances is less than the low threshold of the predetermined tolerance. Repositioning may include rotating the inner surface about an axis 1704 (see FIG. 17), which can extend generally along the length of the bone implant image 1302, such that rotation can move one end (for instance one of the top and bottom ends 1308 and 1310) closer to the bone image 1002, while moving a second end (for instance the other of the top and bottom ends 1308 and 1310) away from the bone image 1002. Further, repositioning may include moving at least a portion of the inner surface 1304 (for instance both the top and bottom ends 1308 and 1310) toward bone image 1002 so at decrease at least one of the plurality of distances, for instance when at least one of the distances is greater than the high threshold of the predetermined tolerance. The bone implant image may be updated by repositioning the inner surface in accordance with the changed distance (step 314).

Figure 17:
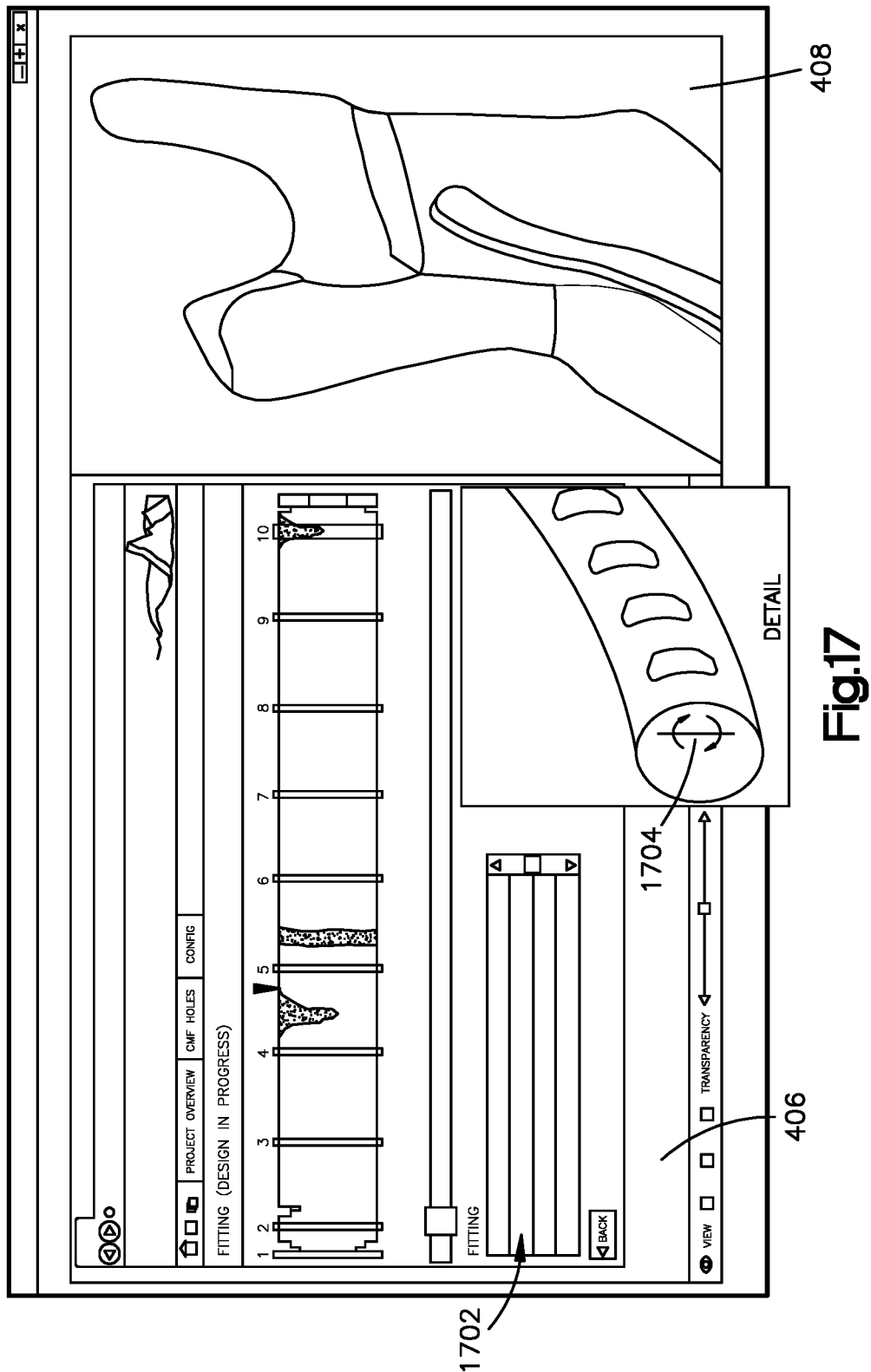

Referring to FIG. 17, the fitting chart 1702 can be manipulated by a user to reposition the inner surface 1304 by rotating, for instance tilting, the bone implant image 1302 about the axis 1704. The fitting chart 1702 may include a rotation column that may allow a user to rotate the bone implant image in relation to the bone image 1002. In accordance with the illustrated embodiment, the axis 1704 is vertical, but the axis of rotation can be oriented in any orientation, for instance a horizontal orientation, as desired. For instance, rotating the bone implant image 1302 about a horizontal axis may move the top end 1308 toward the bone image 1002 while moving the bottom end 1310 away from the bone image 1002, or visa-versa. Similarly, for example, rotating the bone implant image 1302 about a vertical axis may move a first opposed end 1312 toward the bone image 1002 while moving the other opposed end 1314 away from the bone image 1002, or visa-versa.

Figure 18:
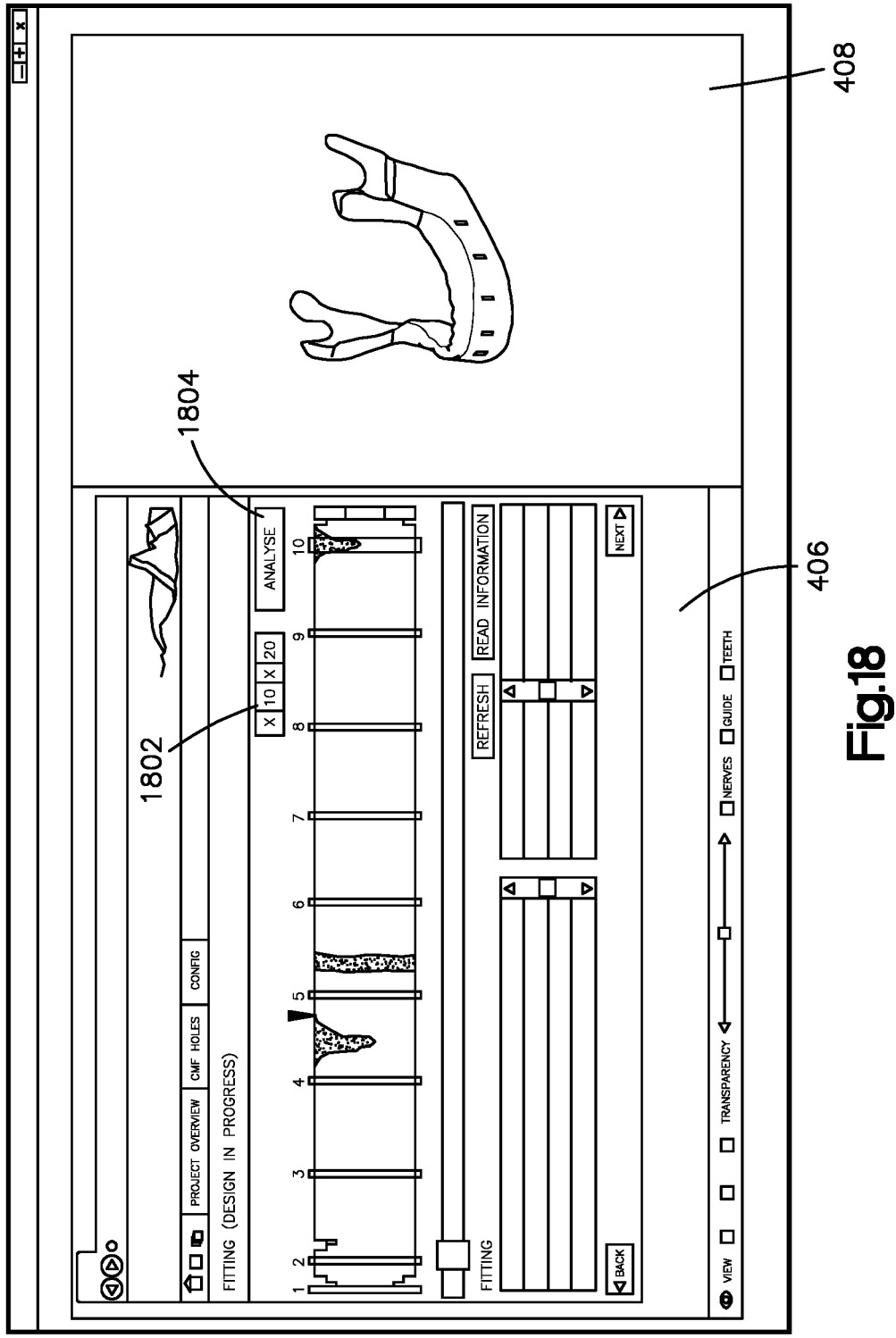

Referring to FIG. 18, the bone implant application can provide for an adjustable resolution 1802 of the fitting matrix 1600 so as to provide greater or less detail of abnormally spaced regions (e.g., too close or too far from the bone image 1002). After the resolution is adjusted, the user may actuate the analyze input 1804, which can be a button or other input, to create a new fitting matrix in accordance with the adjusted resolution 1802.

Figure 19:
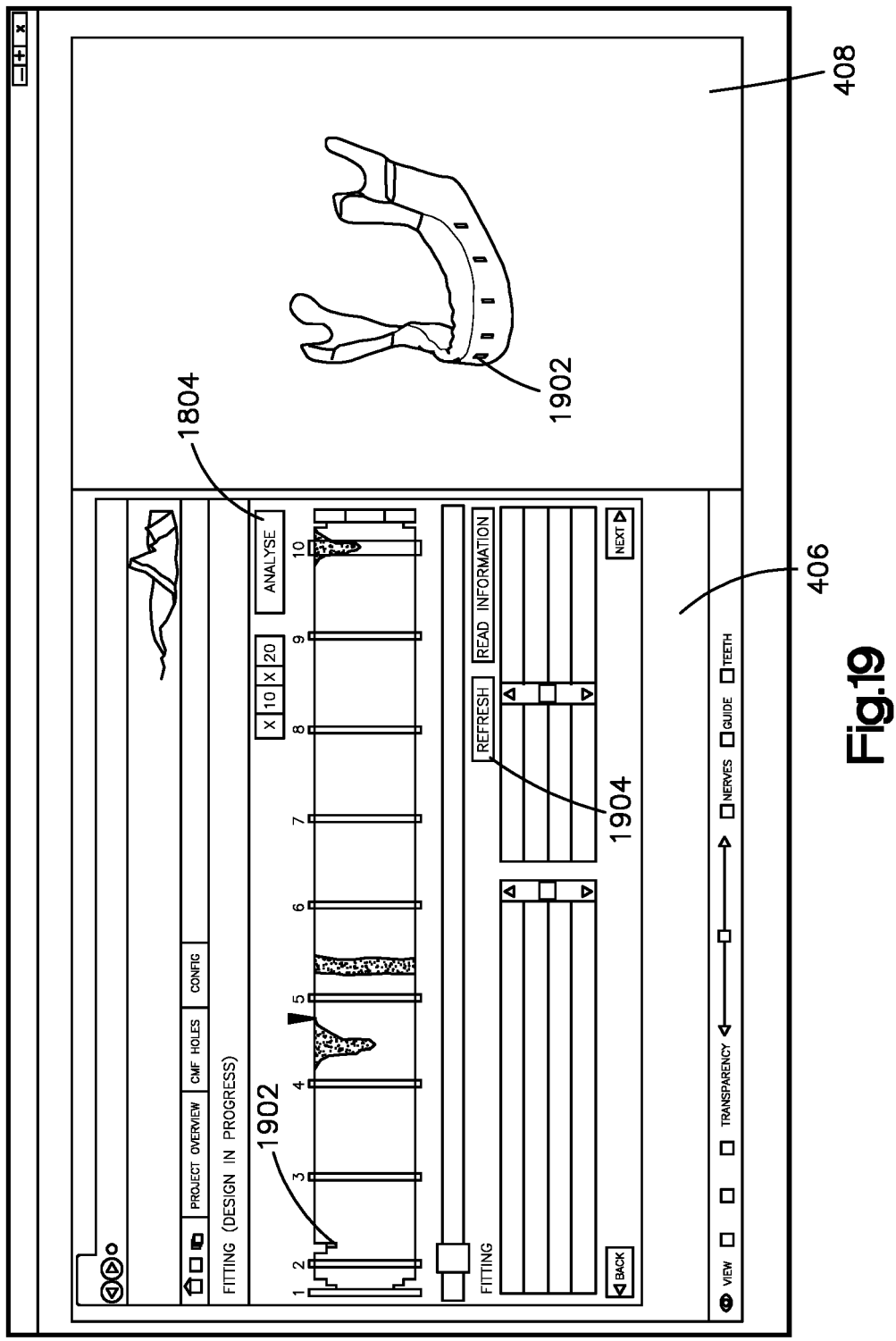
Figure 20:
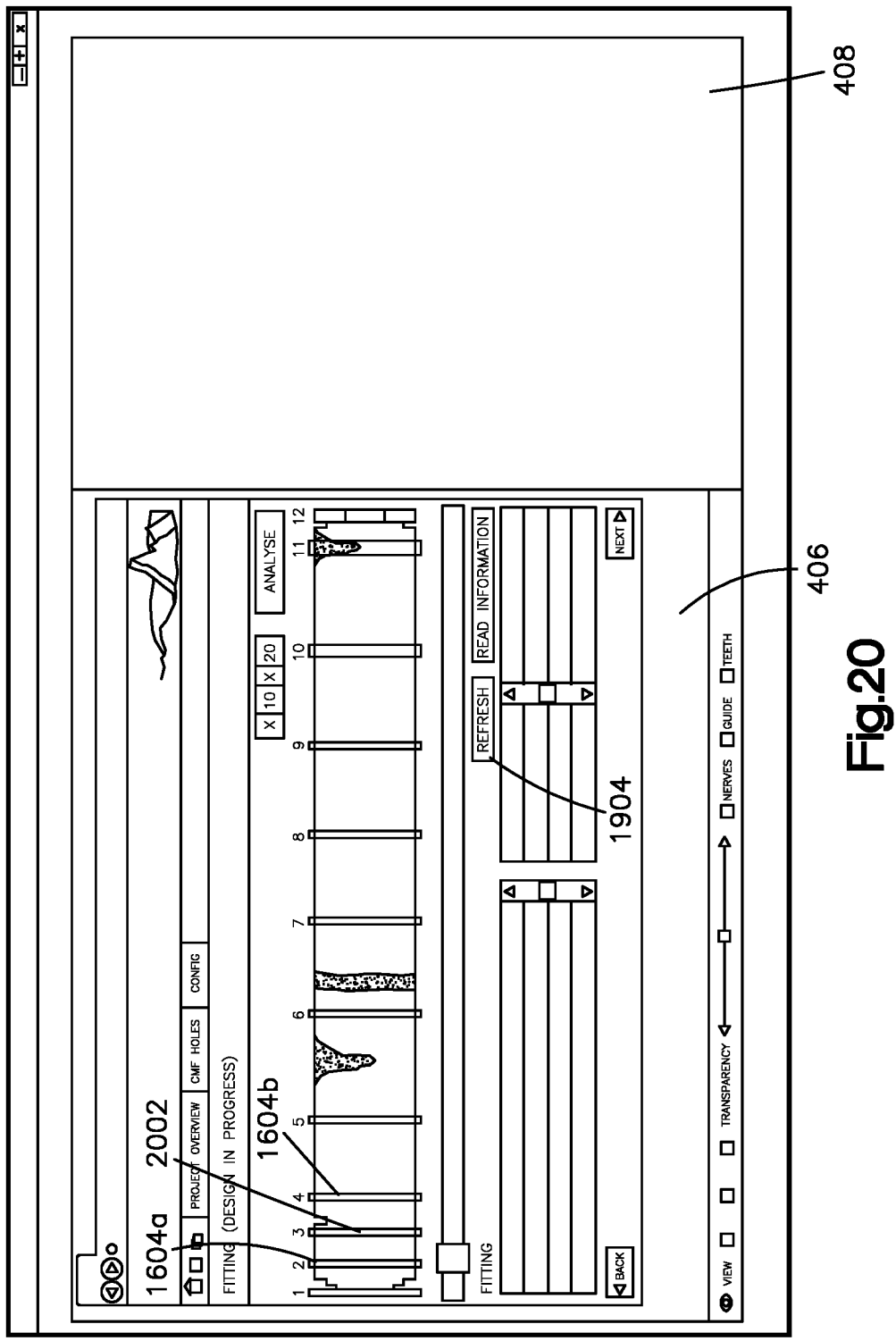

Referring to FIG. 20, the abnormally spaced region of the bone implant image 1302 can be repositioned by defining a new slice 2002 in the bone implant image 1302. For instance, as depicted in FIG. 19, the user may identify a location 1902 on the fitting matrix 1600 that has a distance that is outside of the predetermined tolerance. As shown in FIG. 19, a user may place the curser at location 1902 and the corresponding location 1902 is indicated in corresponding superimposition 1303 that is displayed in the 3-D window 408. In an example embodiment, the new slice 2002 may be calculated when a user clicks on the location 1902 with a mouse or keyboard. When the user clicks on the location 1902, the location 1902 can define a new slice location 1902 of the new slice 2002. Similarly, the bone implant image 1302 may be repositioned, and thus data in the fitting chart 1702 may be updated, in accordance with the new slice 2002 when the refresh input 1904, which can be a button or other input, is selected. Thus, the bone implant image 1302, and in particular the inner surface 1304, can be repositioned by adding a new slice location to define a new slice.

Figure 21:
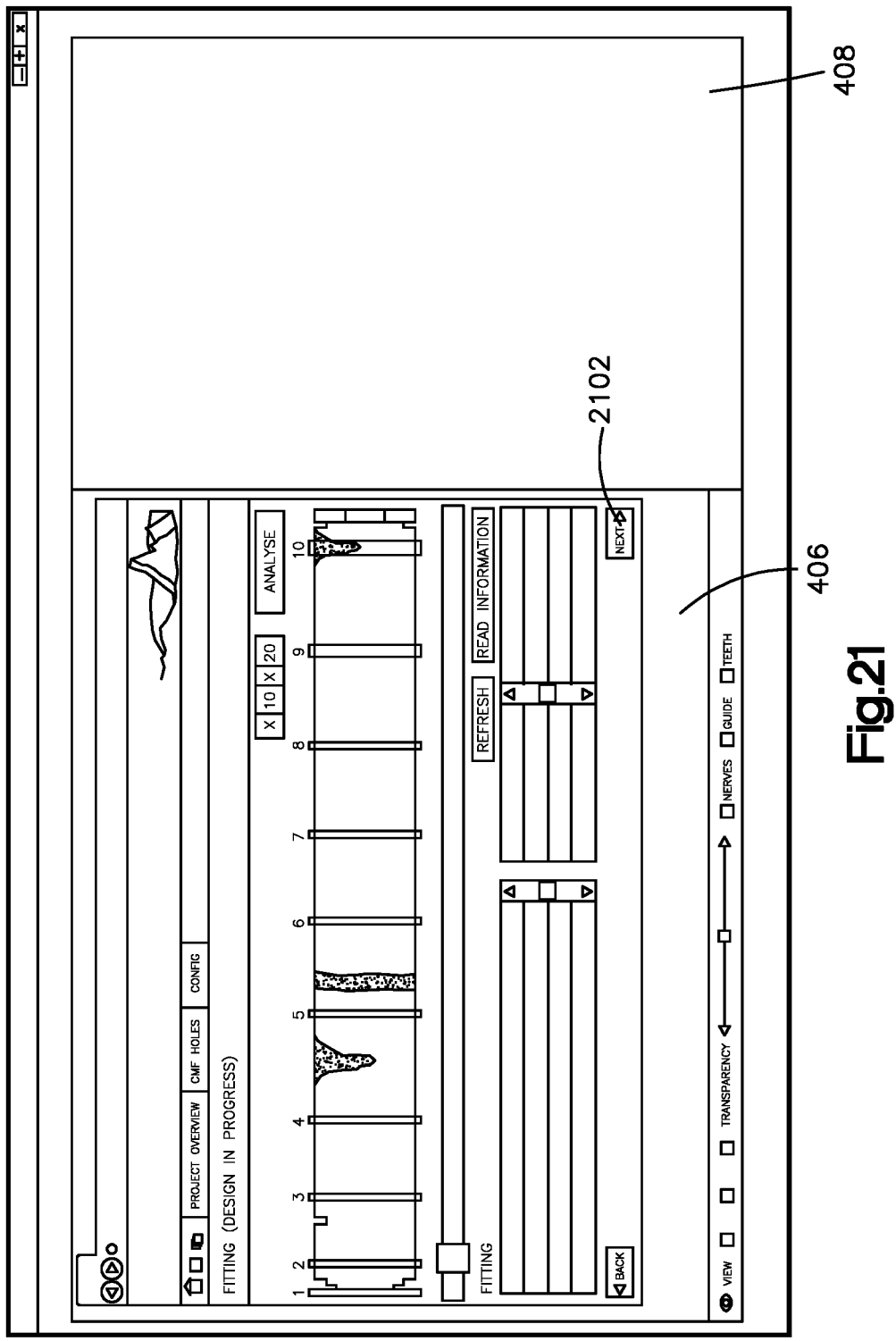

For instance, the new slice 2002 may be fitted to the bone image 1002 so as to define the bone offset 1214 at the new slice 2002. The user may then again actuate the analyze input 1804, which can be a button or other input, to create a new fitting matrix (see FIG. 20) in accordance with the new slice 2002. Thus, the bone implant application can sweep along the bone implant image 1302 between the new slice 2002 and the slices 1604 that are adjacent to the new slice 2002, shown as slices 1604a and 1604b in FIG. 20, and compare the bone offset 1214 to the bone offset tolerance at the newly swept locations. As shown in FIGS. 20 and 21, the location of the bone implant image 1302 at the new slice 2002 and adjacent the new slice 2002 can be spaced further from the bone image 1002 than the spacing prior to introducing the new slice. For instance, the effect of the new slice 2002 may be to move at least a portion of the inner surface 1304 away from the bone image 1002 so as to increase at least one of the distances at locations between the new slice 2002 and the adjacent slices 1604a and 1604b with respect to the bone image 1002. Similarly, the effect of the new slice 2002 may be to move at least a portion of the inner surface 1304 toward the bone image 1002 so as to decrease at least one of the distances at locations between the new slice 2002 and the adjacent slices 1604a and 1604b. It will be understood that any number of slices may be selected as desired, and it will be understood that the slices can be selected at any location of the bone implant image as desired. Once the fitting matrix is acceptable, for instance, the user can select the next input 2102, which can be a button or other input, as shown in FIG. 21.

Figure 22:
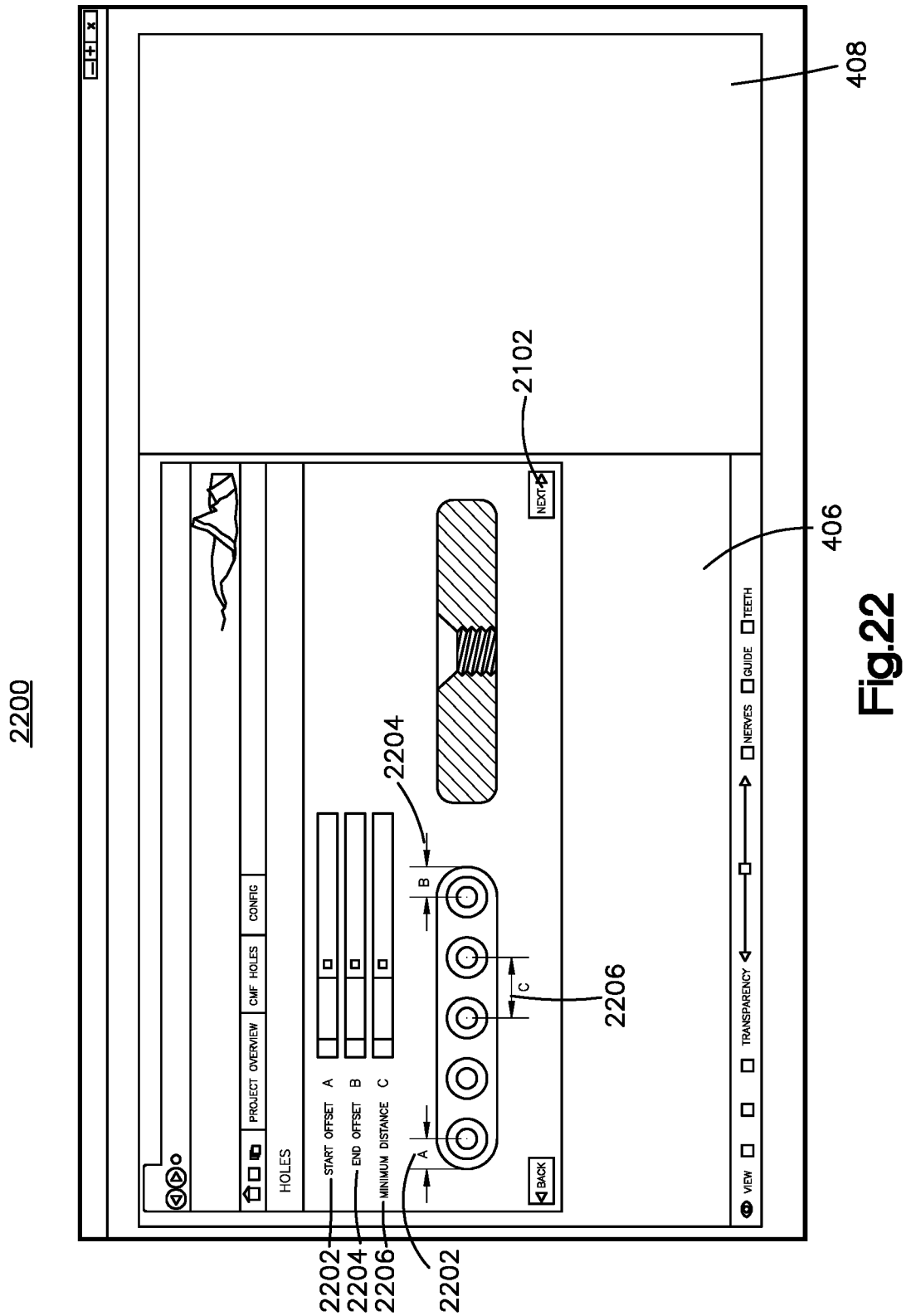
FIG. 22 is a screen shot of an example hole selection page.

Referring to FIG. 22, the bone implant application can further display a hole selection page 2200 that allows a user to select the types of holes that will be included in the bone implant so that the bone implant can be affixed to the bone. Thus, the bone implant application is configured to design bone fixation holes that extend through a bone implant body portion of the bone implant image 1302. For example, holes may be threaded, unthreaded, or partially threaded. The holes may be angled, for instance converge or diverge, along the thickness of the bone implant between the outer surface 1306 and the inner surface 1304, or the holes may be substantially perpendicular to both the outer surface 1306 to the inner surface 1304, or can have one or more converging or diverging regions. It will be understood that the options for the holes are not limited to the options that are illustrated in FIG. 22, and any hole may be offered for selection as desired.

The user can further select the placement of the holes on the hole selection page 2200. For example, a user may select a start offset 2202 which may correspond to the distance from a first end of the bone implant image 1302 that a hole is placed. The user may select an end offset 2204 which may correspond to the distance from a second end of the bone implant image 1302 that a hole is placed. Further, a user may select a minimum distance 2206 in which the holes will be spaced apart from each other along the length of the bone implant. In addition, or alternatively, a user may use the cursor to place each hole on a respective location of the bone implant. It will be understood that the hole selection page 2200 may allow any mechanism for placing holes as desired.

Figure 23:
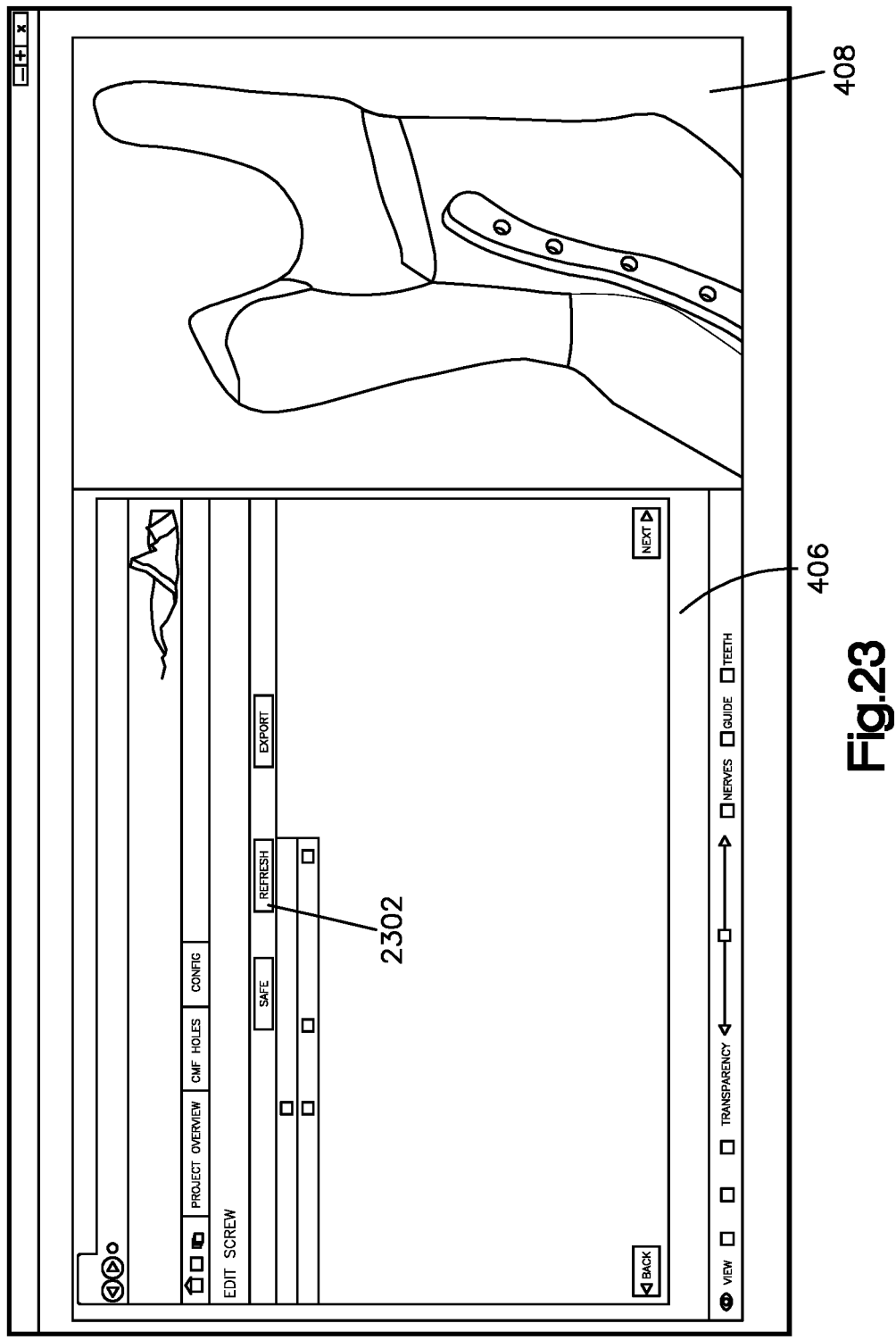
FIG. 23 is a screen shot of an example refresh hole page.
Figure 24:
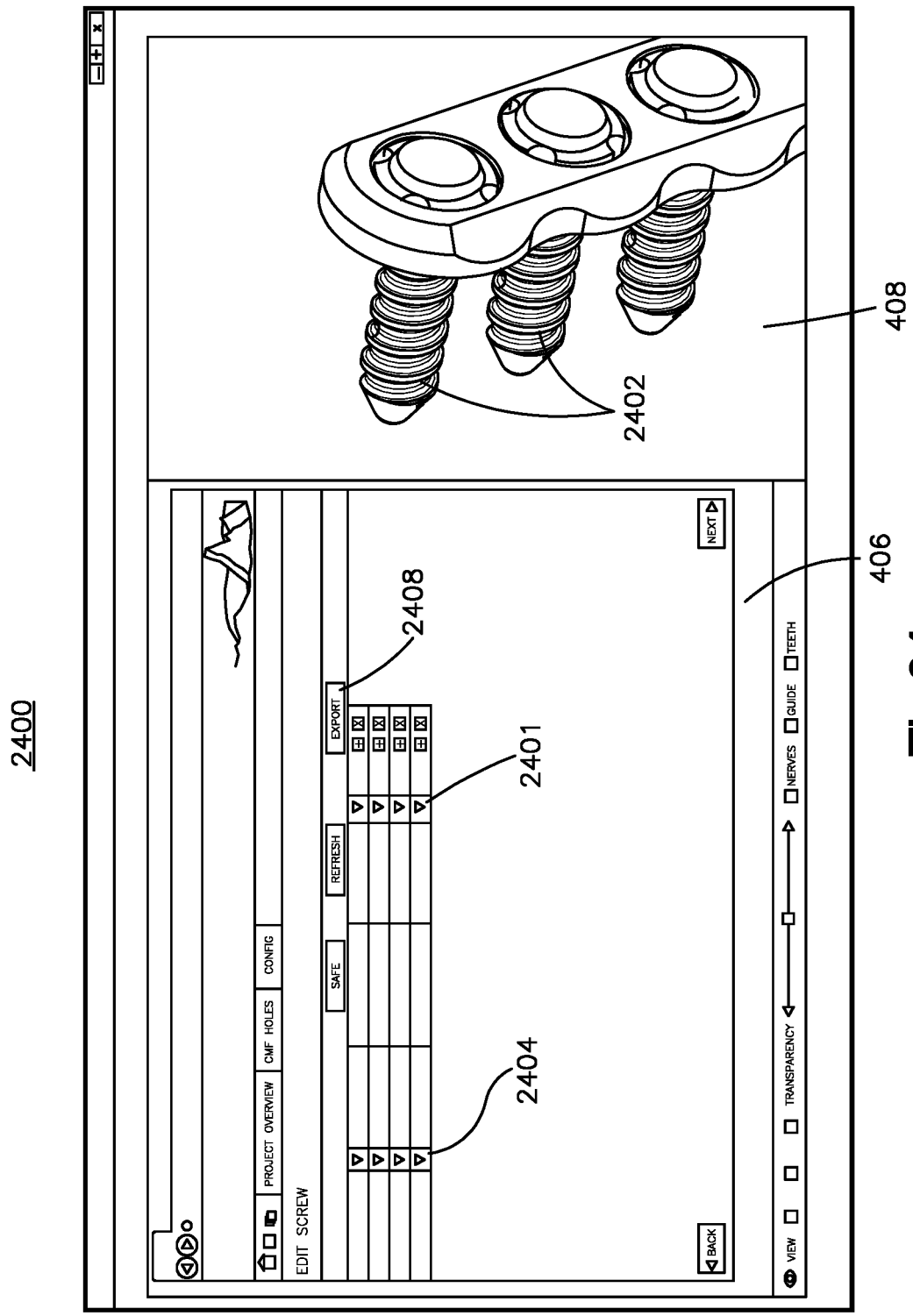
FIG. 24 is a screen shot of an example screw selection page.

Referring to FIG. 23, a user may update the bone implant image 1302 to include the desired holes by selecting the refresh hole input 2302, which can be a button or other input. Referring also to the screw selection page 2400 of FIG. 24, the bone implant application may determine list of screws in accordance with the holes 2404. For example, drop down menus 2401 may display each screw that can be used for each hole 2404. When a user selects a screw in the browser window 406, corresponding screws 2402 may appear in the superimposition 1303 in the 3-D window 408. Thus, the superimposition 1303 may facilitate selection of the screws. For instance, the software and/or a user may determine whether screws 2402 interfere with each other, nerves, teeth, or the like. Further, the screw selection page 2400 may provide a graphical indication, such as a warning sign, if the screws intersect with each other or with another structure that the user may wish to avoid (e.g., nerves, teeth, specific soft tissue, etc.). As shown in the illustrated embodiment, a user may select screws of various lengths, various types, and various angles. It will be appreciated that the screw selection page can offer selection of screws based on any parameters as desired. After screw selection is complete, a user may select the export drawing input 2408, which can be a button or other input, to create a drawing, such as the drawing 2500 shown in FIG. 25. Referring to FIG. 26, a user may select the finish input 2602, which can be a button or other input, when a bone implant design is complete.

Figure 25:
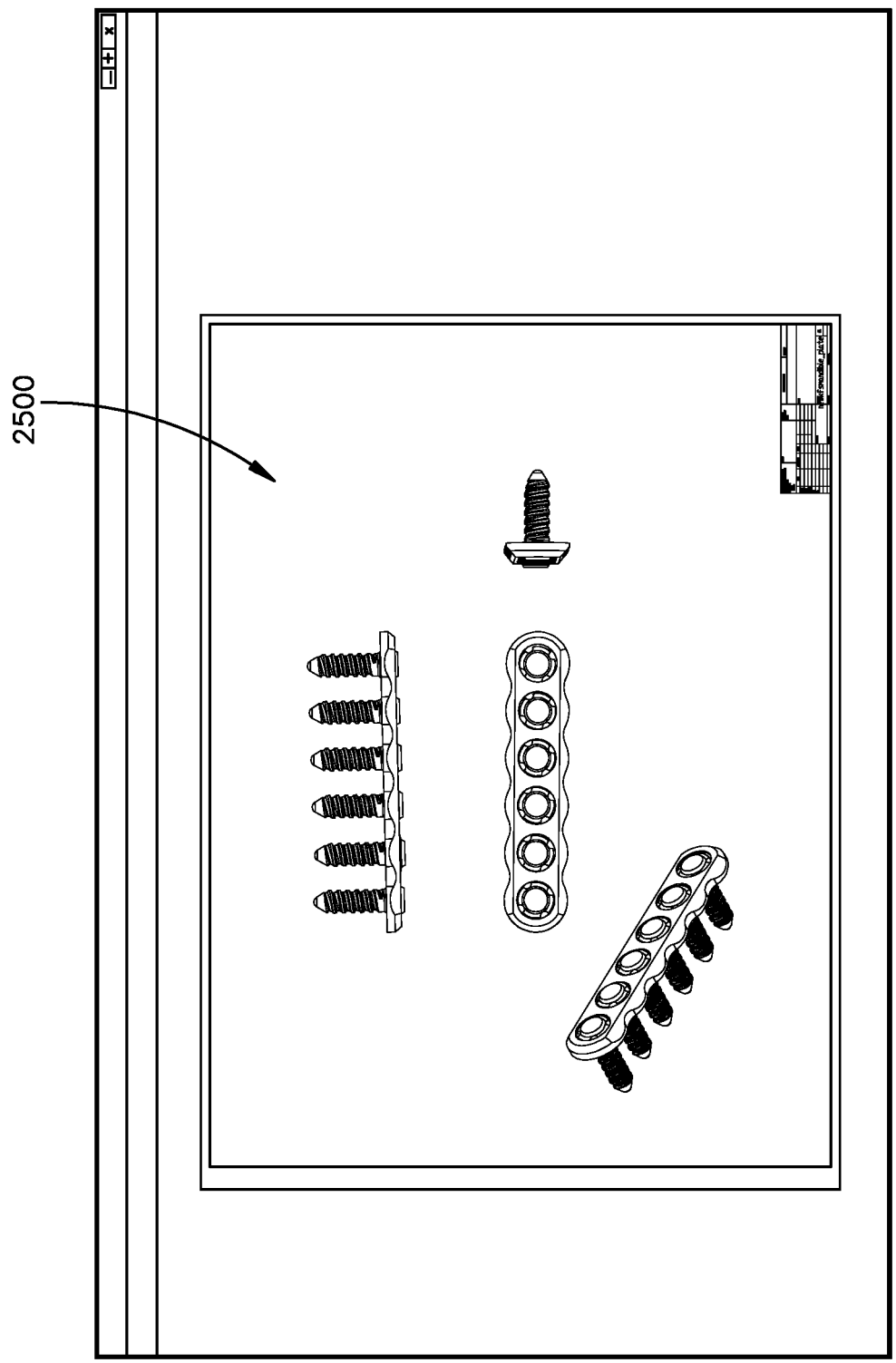
FIG. 25 is a screen shot of an example exported drawing in accordance with a design of a bone implant.
Figure 26:
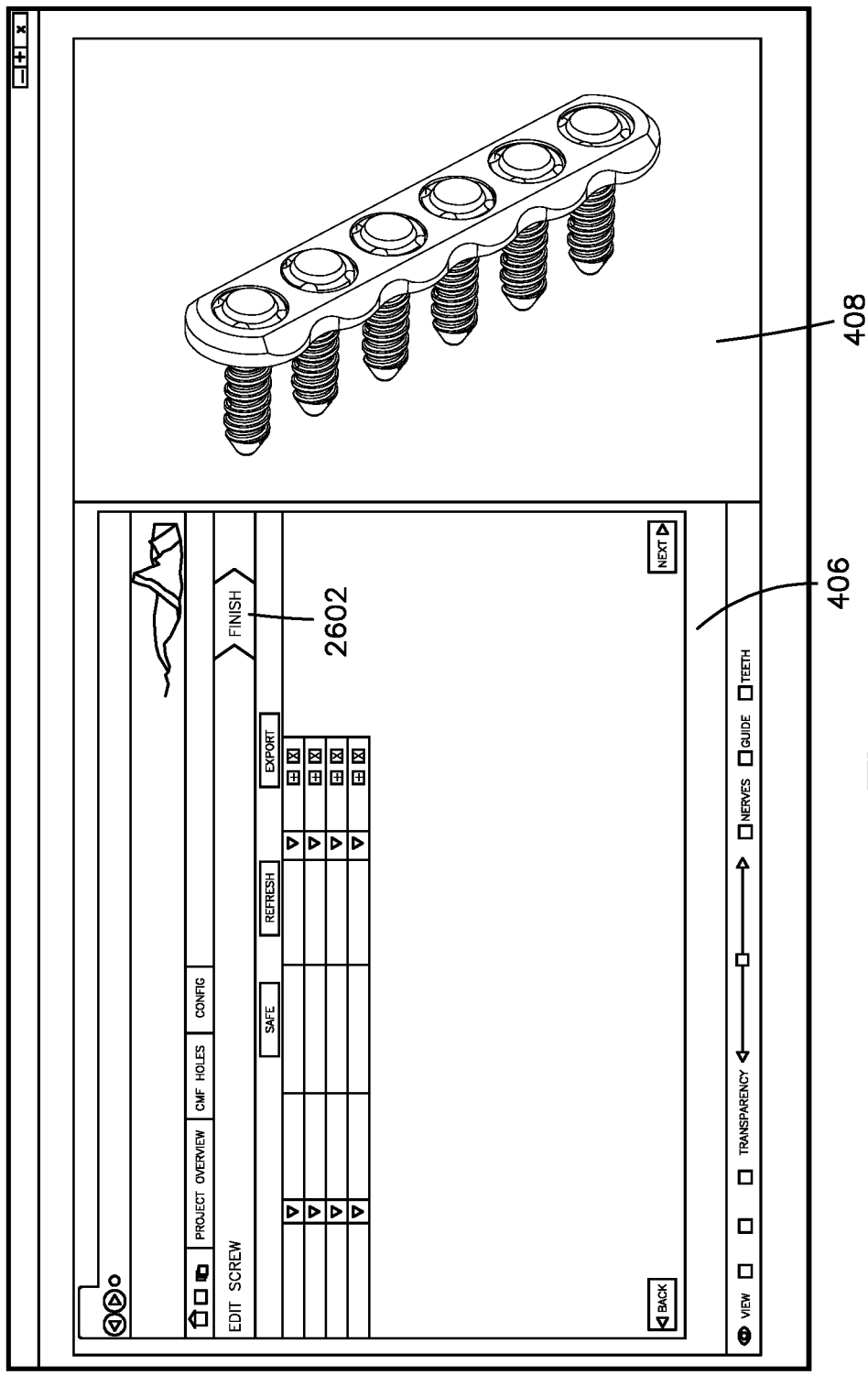
FIG. 26 is a screen shot of an example finish bone implant design page.

The drawing of FIG. 25 can be exported to a bone implant manufacturer. In an example embodiment, the bone implant application may convert the final bone implant design to manufacturing data when the finish input 2602, which can be a button or other input, is actuated. For instance the manufacturing data can be converted to an American Standard Code for Information Interchange (ANSCII) format, although it will be understood that the manufacturing data can be converted into any format as desired. The manufacturing data that is associated with the bone implant image may be sent to a manufacturer (step 316). In an example embodiment, the manufacturing data may be automatically sent to a manufacturer upon completion of the bone implant design, for instance via the network in FIG. 2.

Figure 27:
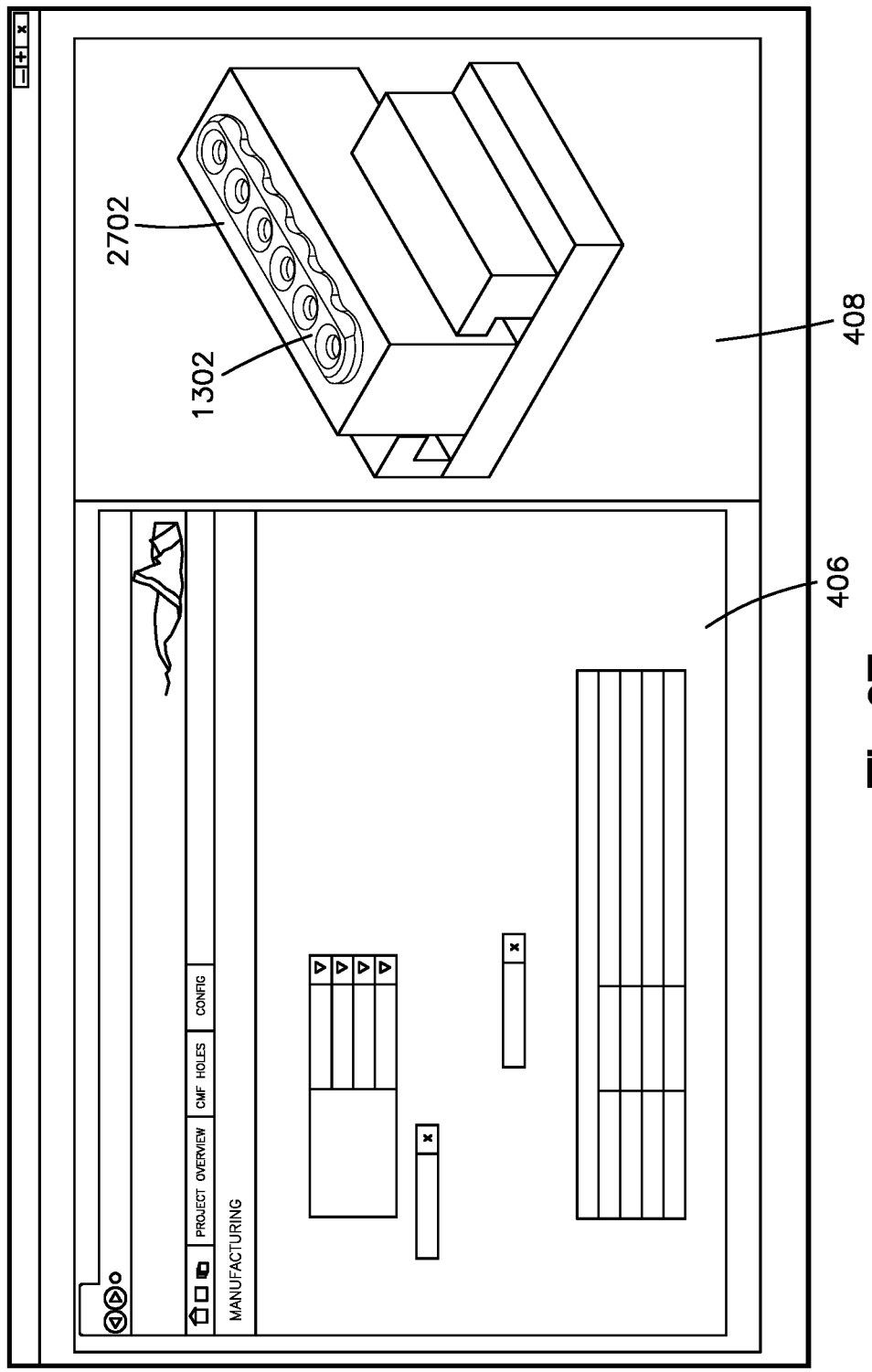
FIG. 27 is a screen shot of an example manufacturing design page.

The manufacturer may receive the data that is associated with the final bone implant image. The manufacturer may fabricate a bone implant in accordance with the received data (step 318). Referring to FIG. 27, a user may select a raw material, represented by the raw material image 2702. For instance, the bone implant image 1302 may be positioned in the image of raw material 2702, and repositioned within the image of the raw material 2072, for instance to ensure that adequate margins exist in the image of the raw material 2072 for manufacture of the bone implant image 1302. The fabrication may include shaping a raw material based on the image of raw material using the tools that were identified as being suitable to manufacture the various corresponding regions of the bone implant on the bone implant image 1302 (see, e.g., description above with reference to FIGS. 13-14).

While example embodiments of devices for executing the disclosed techniques are described herein, the underlying concepts can be applied to any computing device, processor, or system capable of communicating and presenting information as described herein. The various techniques described herein can be implemented in connection with hardware or software or, where appropriate, with a combination of both. Thus, the methods and apparatuses described herein can be implemented, or certain aspects or portions thereof, can take the form of program code (i.e., instructions) embodied in tangible non-transitory storage media, such as floppy diskettes, CD-ROMs, hard drives, or any other machine-readable storage medium (computer-readable storage medium), wherein, when the program code is loaded into and executed by a machine, such as a computer, the machine becomes an apparatus for performing the techniques described herein. In the case of program code execution on programmable computers, the computing device will generally include a processor, a storage medium readable by the processor (including volatile and non-volatile memory and/or storage elements), at least one input device, and at least one output device, for instance a display. The display can be configured to display visual information. For instance, the displayed visual information can include an anatomical image, a bone image, and a graphical indication of the comparison of the distances to the tolerance. Further, the graphical indication can include 1) a first indication when a distance is greater than the high threshold, and 2) a second indication different than the first indication when a distance is less than the low threshold. The program(s) can be implemented in assembly or machine language, if desired. The language can be a compiled or interpreted language, and combined with hardware implementations.

The techniques described herein also can be practiced via communications embodied in the form of program code that is transmitted over some transmission medium, such as over electrical wiring or cabling, through fiber optics, or via any other form of transmission. When implemented on a general-purpose processor, the program code combines with the processor to provide a unique apparatus that operates to invoke the functionality described herein. Additionally, any storage techniques used in connection with the techniques described herein can invariably be a combination of hardware and software.

While the techniques described herein can be implemented and have been described in connection with the various embodiments of the various figures, it is to be understood that other similar embodiments can be used or modifications and additions can be made to the described embodiments without deviating therefrom. For example, it should be appreciated that the steps disclosed above can be performed in the order set forth above, or in any other order as desired. Further, one skilled in the art will recognize that the techniques described in the present application may apply to any environment, whether wired or wireless, and may be applied to any number of such devices connected via a communications network and interacting across the network. Therefore, the techniques described herein should not be limited to any single embodiment, but rather should be construed in breadth and scope in accordance with the appended claims.

What is claimed:

1. A method comprising the steps of:
receiving an anatomical image representative of an anatomical structure;
generating an implant image associated with the anatomical structure, the implant image defining an inner surface that faces the anatomical image, and a plurality of slice locations spaced apart along a length of the implant image, each slice location defining a respective slice of the implant image that is fitted to the anatomical image;
determining a plurality of distances measured from respective locations of the inner surface to the anatomical image, the distances representative of a superimposition of the implant image over the anatomical image, wherein the respective locations comprise locations between the slices that are fitted to the anatomical image;
comparing the distances to a tolerance;
when at least a select one of the plurality of distances is not within the tolerance, repositioning the inner surface so as to change the at least select one of the plurality of distances, wherein repositioning comprises adding a new slice location to define a new slice of the implant image that is fitted to the anatomical image; and
converting the implant image having the new slice location into manufacturing instructions for fabricating an implant.

2. The method as recited in claim 1, further comprising the step of updating the implant image by repositioning the inner surface in accordance with the changed one of the plurality of distances.

3. The method as recited in claim 1, wherein the repositioning step further comprises the step of moving at least a portion of the inner surface away from the anatomical image so as to increase the at least select one of the plurality of distances.

4. The method as recited in claim 1, wherein the repositioning step further comprises the step of moving at least a portion of inner surface toward the anatomical image so as to decrease the at least select one of the plurality of distances.

5. The method as recited in claim 1, wherein the repositioning step further comprises the step of rotating the inner surface about an axis.

6. The method as recited in claim 1, the method further comprising a step of receiving a user-selected offset number, wherein a number of slice locations is based on the user-selected offset number.

7. The method as recited in claim 1, the method further comprising the steps of:
identifying a plurality of cutting instruments; and
determining whether each of the plurality of cutting instruments are capable of producing an implant in accordance with the implant image.

8. The method as recited in claim 7, the method further comprising the steps of:
identifying one or more regions of the implant image;
determining whether each of the plurality of cutting instruments are capable of producing each of the regions in accordance with the implant image; and
selecting, for each region, a preferred cutting instrument that is capable of producing the region.

9. The method as recited in claim 1, the method further comprising the step of generating a graphical indication of the comparison of the distances to the tolerance.

10. The method as recited in claim 9, wherein the tolerance defines a low threshold and a high threshold, the graphical indication comprising 1) a first indication when a distance is greater than the high threshold, and 2) a second indication different than the first indication when a distance is less than the low threshold.

11. The method as recited in claim 1, the method further comprising the step of fabricating the implant in accordance with the manufacturing instructions converted from the implant image having the new slice location.

12. The method as recited in claim 1, the method further comprising:
sweeping between slices that are adjacent to each other so as to measure the plurality of distances from respective locations of the inner surface to the anatomical image.

13. The method as recited in claim 1, the method further comprising:
sweeping between the new slice and at least one slice that is adjacent to the new slice so as to measure distances from respective locations that are between the new slice and the at least one slice that is adjacent to the new slice.

14. One or more non-transitory computer-readable storage media having collectively stored thereon instructions that, upon execution by one or more processors of a computer system, cause the computer system to at least:
receive an anatomical image representative of an anatomical structure;
generate an implant image associated with the anatomical structure, the implant image defining an inner surface that faces the anatomical image, and a plurality of slice locations spaced apart along a length of the implant image, each slice location defining a respective slice of the implant image that is fitted to the anatomical image;
determine a plurality of distances measured from respective locations of the inner surface to the anatomical image in respective straight lines, the distances representative of a superimposition of the implant image over the anatomical image, wherein the respective locations comprise locations between the slices that are fitted to the anatomical image;
compare the distances to a tolerance;
when at least a select one of the plurality of distances is not within the tolerance, reposition the inner surface so as to change the at least select one of the plurality of distances, wherein the reposition comprises adding a new slice location to define a new slice of the implant image that is fitted to the anatomical image; and
convert the implant image having the new slice location into manufacturing instructions for fabricating an implant.

15. The non-transitory computer-readable storage media of claim 14, wherein the instructions to reposition the inner surface further comprise instructions that, upon execution by the one or more processors of the computer system, cause the computer system to at least move at least a portion of the inner surface away from the anatomical image so as to increase the at least select one of the plurality of distances.

16. The non-transitory computer-readable storage media of claim 14, wherein the instructions to reposition the inner surface further comprise instructions that, upon execution by the one or more processors of the computer system, cause the computer system to at least move at least a portion of inner surface toward the anatomical image so as to decrease the at least select one of the plurality of distances.

17. The non-transitory computer-readable storage media of claim 14, having further stored thereon instructions that, upon execution by the one or more processors of the computer system, cause the computer system to at least:
identify a plurality of cutting instruments;
identify one or more regions of the implant image;
determine whether each of the plurality of cutting instruments are capable of producing each of the regions in accordance with the implant image; and
select, for each region, a preferred cutting instrument that is capable of producing the region.

18. A computer system comprising:
a processor;
a display coupled to the processor, the display configured to display visual information comprising an anatomical image and an implant image; and
a memory in communication with the processor, the memory having stored therein instructions that, upon execution by the processor, cause the computer system to perform operations comprising:
receiving the anatomical image representative of an anatomical structure;
generating the implant image associated with the anatomical structure, the implant image defining an inner surface that faces the anatomical image, and a plurality of slice locations spaced apart along a length of the implant image, each slice location defining a respective slice of the implant image that is fitted to the anatomical image;
determining a plurality of distances measured from respective locations of the inner surface to the anatomical image, the distances representative of a superimposition of the implant image over the anatomical image, wherein the respective locations comprise locations between the slices that are fitted to the anatomical image;
comparing the distances to a tolerance;
when at least a select one of the plurality of distances is not within the tolerance, repositioning the inner surface so as to change the at least select one of the plurality of distances, wherein repositioning comprises adding a new slice location to define a new slice of the implant image that is fitted to the anatomical image; and converting the implant image having the new slice location to manufacturing instructions for fabricating an implant.

19. The computer system as recited in claim 18, wherein the visual information further comprises a graphical indication of the comparison of the distances to the tolerance.

20. The computer system as recited in claim 19, wherein the tolerance defines a low threshold and a high threshold, the graphical indication comprising 1) a first indication when a distance is greater than the high threshold, and 2) a second indication different than the first indication when a distance is less than the low threshold.

* * * * *